United States Patent
Nishiyama et al.

(10) Patent No.: US 7,408,084 B2
(45) Date of Patent: Aug. 5, 2008

(54) PROCESS FOR PRODUCING OPTICALLY ACTIVE β-AMINO ALCOHOL

(75) Inventors: Akira Nishiyama, Hyogo (JP); Narumi Kishimoto, Hyogo (JP); Nobuo Nagashima, Hyogo (JP)

(73) Assignee: Kaneka Corporation, Osaka (JP)

( * ) Notice: Subject to any disclaimer, the term of this patent is extended or adjusted under 35 U.S.C. 154(b) by 217 days.

(21) Appl. No.: 10/516,469

(22) PCT Filed: Jun. 2, 2003

(86) PCT No.: PCT/JP03/06959

§ 371 (c)(1),
(2), (4) Date: Dec. 3, 2004

(87) PCT Pub. No.: WO03/104186

PCT Pub. Date: Dec. 18, 2003

(65) Prior Publication Data

US 2005/0277791 A1      Dec. 15, 2005

(30) Foreign Application Priority Data

Jun. 11, 2002    (JP)    ............................ 2002-170453

(51) Int. Cl.
*C07C 211/05*    (2006.01)
*C07C 213/08*    (2006.01)

(52) U.S. Cl. ................. 564/336; 564/342; 564/343

(58) Field of Classification Search ................. 564/336, 564/342, 343

See application file for complete search history.

(56) References Cited

U.S. PATENT DOCUMENTS 6,114,523 A * 9/2000 Allegrini et al. ............ 540/491

6,255,522 B1 * 7/2001 Matsuo et al. ................. 560/9
2004/0030144 A1    2/2004 Tsunoda et al.

FOREIGN PATENT DOCUMENTS

| DE | 827950 A1 | 1/1952 |
| DE | 927690 A1 | 5/1955 |
| EP | 1142864 A1 | 10/2001 |
| GB | 1413930 A | 11/1975 |

OTHER PUBLICATIONS

Muller, V. H. K. et al, "Beziehungen zwischen Substituenteneinfluβ und Reaktionsbedingungen bei der Reduktion recemischer α-(Phenylalkylamino)- propiophenone mit verschiedenen Kryptobasen" Journal füer praktische Chemie, 1973, vol. 315, No. 3, pp. 449 to 462.

Hwang, G. I. et al, An Efficient Synthesis of Both Enantiomers of Cathinone by Regioselective Reductive Ring Opening of Substituted Aziridines', Tetrahedron, 1996, vol. 52, No. 37, pp. 12111 to 12116, particularly, examples.

Sreekumar, R. et al, "Asymmetric Synthesis of Amines by the Reductive Amination of Ketones Using (+) and (−) Norephedrine Followed by Periodated Oxidation." Tetrahedron Asymmetry, 1993 vol. 4, No. 9, pp. 2095 to 2100, particularly, Sheme 1.

* cited by examiner

*Primary Examiner*—Shailendra Kumar
(74) *Attorney, Agent, or Firm*—Sughrue Mion, PLLC

(57) ABSTRACT

A process for easily producing an optically active β-amino alcohol useful as a pharmaceutical intermediate from an inexpensive, readily available starting material is provided. A readily available α-substituted ketone is reacted with an optically active amine to yield a diastereomer mixture of an optically active α-substituted aminoketone. One of the diastereomers is isolated optionally after the diastereomers are converted to salts with an acid. The optically active α-substituted aminoketone or a salt thereof thus isolated was stereoselectively reduced to yield an optically active β-substituted amino alcohol. The optically active β-substituted amino alcohol is subjected to hydrogenolysis to produce an optically active β-amino alcohol or a salt thereof.

22 Claims, No Drawings

PROCESS FOR PRODUCING OPTICALLY ACTIVE β-AMINO ALCOHOL

This application is a 371 of PCT/JP03/06959 filed Jun. 02, 2003.

TECHNICAL FIELD

The present invention relates to methods for producing optically active 1-aryl-2-amino-1-ethanol derivatives, i.e., optically active β-amino alcohols useful as pharmaceutical intermediates. In particular, it relates to a process for producing an optically active 1-(4-hydroxyphenyl)-2-amino-1-ethanol derivative.

BACKGROUND ART

Conventionally, the following method for producing an optically active β-amino alcohol has been known in the art:

1) producing an α-oxime ketone from ketone and alkyl nitrite; producing a β-oxime alcohol by asymmetric hydrogenation in the presence of a transition metal catalyst; and reducing the oxime group to produce a β-amino alcohol (Japanese Unexamined Patent Application Publication No. 5-4948).

However, this method uses explosive alkyl nitrite, which is difficult to handle, to produce explosive α-oxime ketones and is thus not suitable for industrial applications.

As the method for producing an optically active 1-aryl-2-amino-1-ethanol derivative, the following is known in the art:

2) producing a ketone derivative by reacting benzene with an acid chloride of L-alanine and reducing the carbonyl group to produce (1R,2S)-1-phenyl-2-amino-1-propanol((−)-norephedrine) (Japanese Unexamined Patent Application Publication No. 62-209047);

3) producing N,N-dibenzylalaninal from L-alanine, reacting the N,N-dibenzylalaninal with a phenyl magnesium reagent, and performing debenzylation to obtain (1R,2S)-1-phenyl-2-amino-1-propanol((−)-norephedrine) (European Patent No. 288764, U.S. Pat. No. 4,990,669).

However, these methods are limited to the production of the (1R,2S)-1-phenyl-2-amino-1-propanol((−)-norephedrine) and cannot easily be applied to synthesis of optically active 1-aryl-2-amino-1-ethanol derivatives having substituents in the benzene rings.

As the method for producing an optically active 1-(4-hydroxyphenyl)-2-amino-1-ethanol derivative, the following method has been known:

4) producing a salt from tartaric acid and racemic erythro-1-(4-hydroxyphenyl)-2-amino-1-propanol (p-hydroxynorephedrine), followed by separation (J. Med. Chem., 1977, 20, 978).

However, in this method, the racemic mixture to be separated is synthesized through multiple stages, and this method is thus not industrially advantageous. Moreover, expensive D-tartaric acid is necessary in order to obtain (1R,2S)-1-(4-hydroxyphenyl)-2-amino-1-propanol.

DISCLOSURE OF INVENTION

In view of the above, an object of the present invention is to provide a process for easily producing an optically active 1-aryl-2-amino-1-ethanol derivative, in particular, an optically active 1-(4-hydroxyphenyl)-2-amino-1-ethanol derivative, which is useful as a pharmaceutical intermediate, from an inexpensive, readily available starting material.

In view of the above, the present inventors have conducted extensive investigations and have developed a simple method for producing an optically active 1-aryl-2-amino-1-ethanol derivative, in particular, an optically active 1-(4-hydroxyphenyl)-2-amino-1-ethanol derivative, using an inexpensive, readily available starting material.

A first invention is a process for producing an optically active α-substituted aminoketone represented by formula (4):

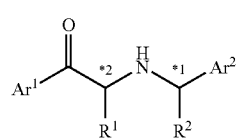

(4)

(wherein $Ar^1$ and $Ar^2$ each independently represent a substituted or unsubstituted $C_6$-$C_{15}$ aryl group, $R^1$ represents a $C_1$-$C_{12}$ alkyl or $C_7$-$C_{12}$ aralkyl group, $R^2$ represents a $C_1$-$C_{12}$ alkyl group, *1 and *2 each represent an asymmetric carbon atom) or an optically active α-substituted aminoketone salt represented by formula (5):

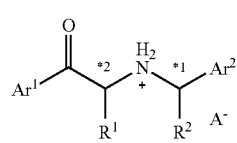

(5)

(wherein $Ar^1$, $Ar^2$, $R^1$, $R^2$, *1, and *2 are the same as above, and $A^−$ represents a counter anion), the process comprising the steps of:

reacting an α-substituted ketone represented by formula (1):

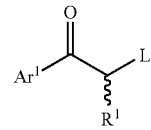

(1)

(wherein $Ar^1$ and $R^1$ are the same as above, and L represents a leaving group) with an optically active amine represented by formula (2):

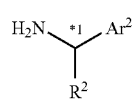

(2)

(wherein $Ar^2$, $R^2$, and *1 are the same as above) to yield a mixture of diastereomers of an optically active α-substituted aminoketone represented by formula (3):

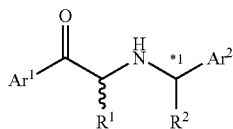

(3)

(wherein $Ar^1$, $Ar^2$, $R^1$, $R^2$, and *1 are the same as above); and isolating one diastereomer from the mixture after optionally yielding salts of the diastereomers with an acid.

A second invention is a process for producing an optically active β-substituted amino alcohol represented by formula (6) or a salt thereof:

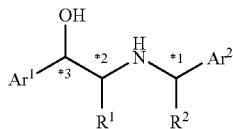

(6)

(wherein $Ar^1$, $Ar^2$, $R^1$, $R^2$, *1, and *2 are the same as above, and *3 represents an asymmetric carbon atom), comprising a step of stereoselectively reducing an optically active α-substituted aminoketone represented by formula (4) above or an optically active α-substituted aminoketone salt represented by formula (5) above.

A third invention is a process for producing an optically active β-amino alcohol represented by formula (7) or a salt thereof:

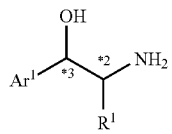

(7)

(wherein $Ar^1$, $R^1$, *2, and *3 are the same as above), comprising the step of hydrogenolyzing an optically active β-substituted amino alcohol represented by formula (6) above or a salt thereof.

A fourth invention is a process of producing an optically active β-amino alcohol represented by formula (7) above or a salt thereof, wherein an optically active α-substituted aminoketone represented by formula (4) above or an optically active α-substituted aminoketone salt represented by formula (5) above is stereoselectively reduced while simultaneously performing the hydrogenolysis.

A fifth invention is a process for isolating an optically active α-substituted aminoketone salt represented by formula (5) above, comprising the steps of yielding salts from an acid and a mixture of diastereomers of an optically active α-substituted aminoketone represented by formula (3) above, and preferentially crystallizing the salt of one diastereomer from a solvent.

A sixth invention is an optically active α-substituted aminoketone represented by formula (4) above wherein $R^1$ is a $C_1$-$C_4$ alkyl group or a $C_7$-$C_{12}$ aralkyl group, or an optically active α-substituted aminoketone salt represented by formula (5) above wherein $R^1$ is a $C_1$-$C_4$ alkyl group or a $C_7$-$C_{12}$ aralkyl group.

A seventh invention is an optically active β-substituted amino alcohol represented by formula (8) or a salt thereof:

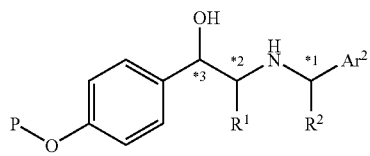

(8)

(wherein $Ar^2$, $R^1$, $R^2$, *1, *2, and *3 are the same as above, and p represents a hydrogen atom or a protecting group protecting the hydroxyl group).

An eighth invention is a process for isolating an optically active β-amino alcohol represented by formula (9) or a salt thereof with an optically inactive acid:

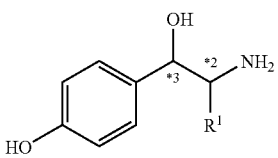

(9)

(wherein $R^1$ represents a $C_1$-$C_{12}$ alkyl or $C_7$-$C_{12}$ aralkyl group, and *2 and *3 each represent an asymmetric carbon atom), comprising a step of crystallizing the optically active β-amino alcohol represented by formula (9) or the salt thereof with the optically inactive acid from an alcohol solvent to remove impurities contained therein to the mother liquor to thereby obtain crystals of the optically active β-amino alcohol represented by formula (9) or the salt thereof with the optically inactive acid.

The present invention will now be described in detail.

First, the compounds used in the present invention and the compounds produced by the present invention are described.

The α-substituted ketone used in the first invention is represented by formula (1) below:

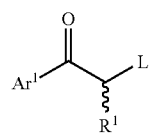

(1)

In the formula, $Ar^1$ represents a substituted or unsubstituted $C_6$-$C_{15}$ aryl group.

Examples of the aryl group include a phenyl group, a naphthyl group, and a biphenyl group. $Ar^1$ is preferably a phenyl group.

Examples of the substituent in $Ar^1$ include halogen atoms, such as fluorine, chlorine, bromine, and iodine atoms, a nitro group, a nitroso group, a cyano group, an amino group, a hydroxyamino group, a $C_1$-$C_{12}$ alkylamino group, a $C_1$-$C_{12}$ dialkylamino group, an azido group, a trifluoromethyl group, a carboxyl group, a $C_1$-$C_{12}$ acyl group, a $C_7$-$C_{12}$ aroyl group, a hydroxyl group, a $C_1$-$C_{12}$ alkyloxy group, a $C_7$-$C_{12}$ aralkyloxy group, a $C_6$-$C_{12}$ aryloxy group, a $C_1$-$C_{12}$ acyloxy group, a $C_7$-$C_{12}$ aroyloxy group, a $C_3$-$C_{12}$ silyloxy group, $C_1$-$C_{12}$ sulfonyloxy groups, and $C_1$-$C_{12}$ alkylthio groups. In particular, a hydroxyl group, a $C_1$-$C_{12}$ alkyloxy group, a $C_7$-$C_{12}$ aralkyloxy group, a $C_1$-$C_{12}$ acyloxy group, $C_7$-$C_{12}$ aroyloxy group, a $C_3$-$C_{12}$ silyloxy group, and a $C_1$-$C_{12}$ sulfonyloxy group are preferred. The number of substituent is 0 to 3.

Preferably, $Ar^1$ is a phenyl group or one of a p-hydroxyphenyl group and a hydroxyl-protected p-hydroxyphenyl group both represented by formula (10):

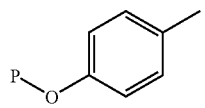

(10)

(wherein P represents a hydrogen atom or a hydroxyl-protecting group).

Examples of the hydroxyl-protecting group include the protecting groups described in Green, Theodora W. *Protective Groups in Organic Synthesis*, 2nd ed.; John Wiley & Sons: 1990, pp. 143-174. In particular, examples of the protecting groups include ether-type protecting groups such as a methyl group, a methoxymethyl group, a benzyloxymethyl group, a methoxyethoxymethyl group, a methylthiomethyl group, a phenylthiomethyl group, a tetrahydropyranyl group, p-bromophenacyl group, an allyl group, an isopropyl group, a cyclohexyl group, and a tert-butyl group; benzyl-type protecting groups such as a benzyl group, a 2,6-dimethylbenzyl group, a 4-methoxybenzyl group, a 2,6-dichlorobenzyl group, a 9-anthranilmethyl group, a diphenylmethyl group, a phenethyl group, and a triphenylmethyl group; silyl-type protecting groups such as a trimethylsilyl group, a triethylsilyl group, and a tert-butyldimethylsilyl group; acyl-type protecting groups, such as an acetyl group, a chloroacetyl group, a trifluoroacetyl group, and a pivaloyl group; aroyl-type protecting groups such as a benzoyl group, a p-methylbenzoyl group, a p-chlorobenzoyl group, an o-chlorobenzoyl group, and a p-nitrobenzoyl group; carbonate-type protecting groups such as methoxycarbonyl group, an ethoxycarbonyl group, a benzyloxycarbonyl group, and a tert-butoxycarbonyl group; phosphinate-type protecting groups such as a dimethylphosphinyl group; and sulfonyl-type protecting groups such as a methanesulfonyl group, an ethanesulfonyl group, a chloromethanesulfonyl group, a trichloromethanesulfonyl group, a benzenesulfonyl group, a p-toluenesulfonyl group, an o-nitrobenzenesulfonyl group, an m-nitrobenzenesulfonyl group, a p-nitrobenzenesulfonyl group, an o-chlorobenzenesulfonyl group, an m-chlorobenzenesulfonyl group, a p-chlorobenzenesulfonyl group, and a trifluoromethanesulfonyl group.

Particularly preferable are benzyl-type protecting groups such as a benzyl group, a 2,6-dimethylbenzyl group, a 4-methoxybenzyl group, a 2,6-dichlorobenzyl group, a 9-anthranilmethyl group, a diphenylmethyl group, a phenethyl group, and a triphenylmethyl group; aroyl-type protecting groups such as a benzoyl group, a p-methylbenzoyl group, a p-chlorobenzoyl group, an o-chlorobenzoyl group, and a p-nitrobenzoyl group; sulfonyl-type protecting groups such as a methanesulfonyl group, an ethanesulfonyl group, a chloromethanesulfonyl group, a trichloromethanesulfonyl group, a benzenesulfonyl group, a p-toluenesulfonyl group, an o-nitrobenzenesulfonyl group, an m-nitrobenzenesulfonyl group, a p-nitrobenzenesulfonyl group, an o-chlorobenzenesulfonyl group, an m-chlorobenzenesulfonyl group, a p-chlorobenzenesulfonyl group, and a trifluoromethanesulfonyl group. Most preferable are a benzyl group, a benzoyl group, and a methanesulfonyl group.

Yet more preferably, $Ar^1$ is a phenyl group, a p-hydroxyphenyl group, a p-benzyloxyphenyl group, p-benzoyloxyphenyl group, or a p-methanesulfonyloxyphenyl group.

$R^1$ represents a $C_1$-$C_{12}$ alkyl group or a $C_7$-$C_{12}$ aralkyl group. Examples of the alkyl group include a methyl group, an ethyl group, an n-propyl group, an isopropyl group, an n-butyl group, an isobutyl group, a sec-butyl group, a tert-butyl group, and an n-hexyl group. Examples of the aralkyl group include a benzyl group and a phenethyl group. $R^1$ is preferably a methyl group or an ethyl group.

L represents a leaving group. Examples of the leaving group include halogen atoms such as fluorine, chlorine, bromine, and iodine atoms; and sulfonyloxy groups such as a methanesulfonyloxy group, an ethanesulfonyloxy group, a chloromethanesulfonyloxy group, a trichloromethanesulfonyloxy group, a benzenesulfonyloxy group, a p-toluenesulfonyloxy group, o-nitrobenzenesulfonyloxy group, an m-nitrobenzenesulfonyloxy group, a p-nitrobenzenesulfonyloxy group, an o-chlorobenzenesulfonyloxy group, an m-chlorobenzenesulfonyloxy group, a p-chlorobenzenesulfonyloxy group, and a trifluoromethanesulfonyloxy group. The leaving group is preferably a halogen atom, and more preferably a chlorine or bromine atom.

The α-substituted ketone (1) can be easily synthesized by halogenation of a precursor ketone using a halogenating agent such as chlorine gas, sulfuryl chloride, or liquid bromine when the precursor ketone is available, or by sulfonylation of a precursor α-hydroxy ketone using a sulfonylating agent, such as methanesulfonyl chloride, p-toluenesulfonyl chloride, or a trifluoromethanesulfonic acid anhydride, when the precursor α-hydroxy ketone is available.

The optically active amine used in the first invention is represented by formula (2):

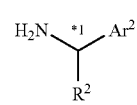

(2)

In the formula, $Ar^2$ represents a substituted or unsubstituted $C_6$-$C_{15}$ aryl group. Examples of the aryl group include a phenyl group, a naphthyl group, and a biphenyl group. A phenyl group is preferred.

Examples of the substituent in $Ar^2$ include halogen atoms, such as fluorine, chlorine, bromine, and iodine atoms, a nitro group, a nitroso group, a cyano group, an amino group, a hydroxyamino group, a $C_1$-$C_{12}$ alkylamino group, a $C_1$-$C_{12}$ dialkylamino group, an azido group, a trifluoromethyl group, a carboxyl group, a $C_1$-$C_{12}$ acyl group, a $C_7$-$C_{12}$ aroyl group, a hydroxyl group, a $C_1$-$C_{12}$ alkyloxy group, a $C_7$-$C_{12}$ aralkyloxy group, a $C_6$-$C_{12}$ aryloxy group, a $C_1$-$C_{12}$ acyloxy group, a $C_7$-$C_{12}$ aroyloxy group, a $C_3$-$C_{12}$ silyloxy group, a $C_1$-$C_{12}$ sulfonyloxy group, and a $C_1$-$C_{12}$ alkylthio group. $Ar^2$ is preferably a $C_1$-$C_{12}$ alkyloxy group. The number of substituent is 0 to 3.

$Ar^2$ is preferably a phenyl group or a p-methoxyphenyl group.

$R^2$ represents a $C_1$-$C_{12}$ alkyl group. Examples of the alkyl group include a methyl group, an ethyl group, an n-propyl group, an isopropyl group, an n-butyl group, an isobutyl group, a sec-butyl group, a tert-butyl group, and an n-hexyl group. $R^2$ is preferably a methyl group.

Furthermore, *1 represents an asymmetric carbon atom.

The optically active α-substituted aminoketone produced by the first invention is represented by formula (4):

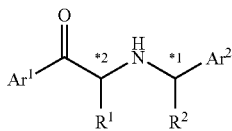

(4)

wherein $Ar^1$, $Ar^2$, $R^1$, $R^2$, and *1 are the same as above and *2 represents an asymmetric carbon atom. Preferably, the optically active α-substituted aminoketone is a compound having $Ar^1$ representing a p-hydroxyphenyl group or a hydroxyl-protected p-hydroxyphenyl group, i.e., a compound represented by formula (11):

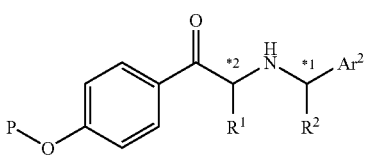

(11)

wherein P represents a hydrogen atom or a hydroxyl-protecting group.

The optically active α-substituted aminoketone salt synthesized by the first invention is represented by formula (5):

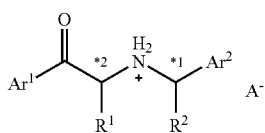

(5)

wherein $Ar^1$, $Ar^2$, $R^1$, $R^2$, *1, and *2 are the same as above.

In the formula, $A^-$ represents a counter anion of a protonic acid, e.g., a methanesulfonate ion, a benzenesulfonate ion, a p-toluenesulfonate ion, a trifluoromethanesulfonate ion, a fluorine ion, a chlorine ion, a bromine ion, an iodine ion, a sulfate ion, a hydrogen sulfate ion, a perchlorate ion, a nitrate ion, a phosphate ion, a formate ion, an acetate ion, a benzoate ion, a propionate ion, an oxalate ion, a citrate ion, an L-tartrate ion, a D-tartrate ion, a meso-tartrate ion, an L-mandelate ion, or a D-mandelate ion. Preferably, $A^-$ is a methanesulfonate ion, a chlorine ion, or a bromine ion. More preferably, the optically active α-substituted aminoketone salt is a compound having $Ar^1$ representing a p-hydroxyphenyl group or a hydroxyl-protected p-hydroxyphenyl group.

In particular, an optically active compound represented by formula (4) or (5) with $R^1$ representing a $C_1$-$C_4$ alkyl group or a $C_7$-$C_{12}$ aralkyl group is a new molecular entity not disclosed in any literature heretofore.

Note that a compound represented by formula (4) or (5) has two asymmetric carbon atoms and thus has four optical isomers. All of these optical isomers are included in the scope of the present invention.

When $A^-$ in formula (5) is a methanesulfonate ion, an isomer having the S absolute configuration at *2 and the R absolute configuration at *1 or an isomer having the R absolute configuration at *2 and the S absolute configuration at *1 are preferred. When $A^-$ in formula (5) is a chlorine ion or a bromine ion, an isomer having the R absolute configuration at *2 and the R absolute configuration at *1 or an isomer having the S absolute configuration at *2 and the S absolute configuration at *1 are preferred.

The optically active β-substituted amino alcohol synthesized by the second invention is represented by formula (6):

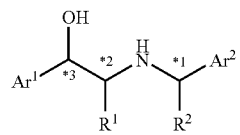

(6)

wherein $Ar^1$, $Ar^2$, $R^1$, $R^2$, *1, and *2 are the same as above, and *3 represents an asymmetric carbon atom. In particular, a compound represented by formula (6) where $Ar^1$ is a p-hydroxyphenyl group or a hydroxyl-protected p-hydroxyphenyl group, i.e., a compound represented by formula (8) below, is a new molecular entity not disclosed in any literature heretofore:

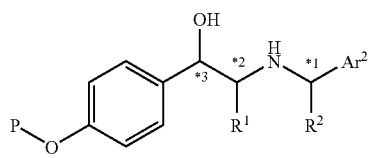

(8)

A compound (8) has three asymmetric carbon atoms and thus eight optical isomers. All of these isomers are within the scope of the present invention.

An isomer having the S absolute configuration at *2, the R absolute configuration at *1, and the R absolute configuration at *3, an isomer having the R absolute configuration at *2, the R absolute configuration at *1, and the S absolute configuration at *3, an isomer having the R absolute configuration at *2, the S absolute configuration at *1, and the S absolute configuration at *3, and an isomer having the S absolute configuration at *2, the S absolute configuration at *1, and the R absolute configuration at *3 are preferred.

The optically active β-amino alcohol synthesized by the third invention is represented by formula (7):

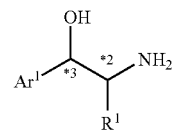

(7)

wherein $R^1$, $Ar^1$, *2, and *3 are the same as above.

$Ar^1$ is preferably a phenyl group or a p-hydroxyphenyl group, and more preferably a p-hydroxyphenyl group.

An optically active compound represented by formula (7) has two asymmetric carbon atoms and thus four optical isomers. All of these optical isomers are in the scope of the present invention.

An isomer having the S absolute configuration at *2 and the R absolute configuration at *3 and an isomer having the R absolute configuration at *2 and the S absolute configuration at *3 are preferred.

The production process of the present invention will now be described.

In the present invention, an α-substituted ketone represented by formula (1) is reacted with an optically active amine represented by formula (2) to produce a diastereomer mixture of an optically active α-substituted aminoketone represented by formula (3).

The reaction between the α-substituted ketone (1) and the optically active amine (2) proceeds in the presence of a base. Although it is possible to conduct the reaction using an excess of the optically active amine (2) functioning also as the base, a less expensive base is preferably used for the reaction.

The molar quantity of the optically active amine used is preferably 0.8 to 5 times and more preferably 1 to 1.5 times that of the α-substituted ketone.

Examples of the base include inorganic salts such as lithium hydroxide, sodium hydroxide, potassium hydroxide, calcium hydroxide, magnesium hydroxide, lithium carbonate, sodium carbonate, potassium carbonate, cesium carbonate, calcium carbonate, magnesium carbonate, lithium hydrogen carbonate, sodium hydrogen carbonate, and potassium hydrogen carbonate; and tertiary amines such as triethylamine, N-methylpiperidine, N-methylmorpholine, pyridine, 2-methylpyridine, 3-methylpyridine, N,N-dimethylaminopyridine, and imidazole. Preferably, the base is an inorganic salt, such as lithium hydrogen carbonate, sodium hydrogen carbonate, or potassium hydrogen carbonate; or a tertiary amine such as triethylamine, N-methylpiperidine, N-methylmorpholine, pyridine, 2-methylpyridine, 3-methylpyridine, N,N-dimethylaminopyridine, and imidazole. More preferably, the base is sodium hydrogen carbonate, triethylamine, or pyridine. The molar quantity of the base is preferably 0.8 to 10 times, and more preferably 1 to 3 times that of the compound (1).

The reaction temperature is preferably −20° C. to 120° C. and more preferably 10° C. to 100° C. in view of reducing the reaction time and increasing the yield.

Examples of the solvent usable in the reaction include hydrocarbon solvents such as hexane, heptane, benzene, and toluene; ether solvents such as diethyl ether, tetrahydrofuran, 1,4-dioxane, methyl tert-butyl ether, and dimethoxyethane; ester solvents such as ethyl acetate, n-propyl acetate, and tert-butyl acetate; ketone solvents such as acetone and methyl ethyl ketone; halogenated solvents such as methylene chloride, chloroform, and 1,1,1-trichloroethane; amide solvents such as dimethylformamide, dimethylacetamide, and N-methylpyrrolidone; nitrile solvents such as acetonitrile and propionitrile; sulfoxide solvents such as dimethylsulfoxide; phosphoric amide solvents such as hexamethylphosphoric triamide; alcohol solvents such as methanol, ethanol, and isopropanol; and water. These solvents may be used alone or in combination. When the solvents are used in combination, the mixing ratio is not particularly limited.

Preferably, the solvent is ethyl acetate, tetrahydrofuran, acetonitrile, dimethylformamide, dimethylsulfoxide, methanol, ethanol, or water. The solvent is more preferably acetonitrile, ethanol, or a mixture of ethanol and water.

The weight of the solvent used is preferably up to 50 times and more preferably 5 to 20 times the weight of the compound (1).

During the reaction, the method of adding the compound (1), the compound (2), the base, and the solvent, and the order of adding these are not particularly limited.

After the reaction, a typical post-treatment may be carried out to obtain the reaction product from the reaction solution. Alternatively, a subsequent process may be performed without carrying out the post-treatment in some cases. An example of the post-treatment is an extraction process. In this extraction process, after the termination of the reaction, the reaction solution is mixed with water, or, if necessary, an alkaline aqueous solution such as aqueous sodium hydroxide, aqueous potassium carbonate, or aqueous sodium hydrogen carbonate, and extraction is performed using a typical extraction solvent, such as ethyl acetate, diethyl ether, methylene chloride, toluene, or hexane. The resulting extract is heated under a reduced pressure to distill off the reaction solvent and the extraction solvent to thereby obtain a diastereomer mixture of an optically active α-substituted aminoketone represented by formula (3).

Typically, an optically pure product is used as the optically active amine (2); hence, the compound (3) is obtained as a mixture of two diastereomers.

A step of preferentially isolating one diastereomer from the diastereomer mixture of the optically active α-substituted aminoketone represented by formula (3) will now be described.

In this step, a typical isolation process conducted based on the differences in physical properties of the diastereomers may be employed. For example, the desired isolation can be carried out by chromatography, such as column chromatography, centrifugal chromatography, thin-layer chromatography, or high-performance liquid chromatography, fractional distillation, or preferential crystallization of a diastereomer from a suitable solvent.

It is also possible to isolate the optically active α-substituted aminoketone salt represented by formula (5) having a particular configuration by preparing a salt of the compound represented by formula (3) with an acid and by preferentially crystallizing the salt of one diastereomer from the solvent. When the isolation efficiency is insufficient after performing the isolation process once, the process may be repeated to isolate one diastereomer.

Examples of the acid include sulfonic acids, such as methanesulfonic acid, benzenesulfonic acid, p-toluenesulfonic acid, and trifluoromethanesulfonic acid; hydrogen halide such as hydrogen fluoride, hydrogen chloride, hydrogen bromide, and hydrogen iodide; inorganic acids such as sulfuric acid, perchloric acid, nitric acid, and phosphoric acid; and carboxylic acids such as formic acid, acetic acid, benzoic acid, propionic acid, oxalic acid, citric acid, L-tartaric acid, D-tartaric acid, meso-tartaric acid, L-mandelic acid, and D-mandelic acid. The acid is preferably a sulfonic acid, such as methanesulfonic acid, benzenesulfonic acid, p-toluenesulfonic acid, or trifluoromethanesulfonic acid; or a hydrogen halide, such as hydrogen fluoride, hydrogen chloride, hydrogen bromide, or hydrogen iodide. The acid is more preferably methanesulfonic acid, hydrogen chloride, or hydrogen bromide. Note that when a hydrogen halide is used, it may be used in the form of gas, a solution of the hydrogen halide in a solvent such as ethyl acetate, methanol, 1,4-dioxane, or tetrahydrofuran, or an aqueous halide acid such as hydrofluoric acid, hydrochloric acid, hydrobromic acid, or hydriodic acid.

The molar quantity of the acid is preferably 0.5 to 2 times, and more preferably 0.8 to 1.2 times that of the compound (3).

As the solvent described above, a solvent having a relatively low boiling point is preferred considering the process of drying wet crystals to remove the solvent or the process of recovering and recycling the solvent (recovery by distillation). In general, examples of these solvents include those having boiling points of about 100° C. or less at 1 atm or less. The solvent is not particularly limited and may be appropriately selected according to the type of the acid used.

When a sulfonic acid, such as methanesulfonic acid, benzenesulfonic acid, p-toluenesulfonic acid, or trifluoromethanesulfonic acid, in particular, methanesulfonic acid, is used, the solvent may be an ester solvent such as ethyl formate, methyl acetate, ethyl acetate, n-propyl acetate, n-butyl acetate, tert-butyl acetate, methyl propionate, ethyl propionate, or γ-butyrolactone; an ether solvent such as diethyl ether, diisopropyl ether, di-n-butyl ether, methyl tert-butyl ether, methyl cyclohexyl ether, dimethoxyethane, diethylene glycol dimethyl ether, tetrahydrofuran, or 1,4-dioxane; a ketone solvent such as acetone, methyl ethyl ketone, diethyl ketone, cyclopentanone, or cyclohexanone; a halogenated solvent such as methylene chloride, chloroform, carbon tetrachloride, 1,2-dichloroethane, or 1,1,1-trichloroethane; an alcohol solvent such as methanol, ethanol, isopropanol, n-butanol, or ethylene glycol; a hydrocarbon solvent such as pentane, petroleum ether, neopentane, hexane, cyclohexane, methylcyclohexane, heptane, cycloheptane, octane, isooctane, benzene, toluene, o-xylene, m-xylene, p-xylene, or ethyl benzene; a nitrile solvent such as acetonitrile or propionitrile; or water. The solvent is preferably ethyl acetate, acetone, or dimethoxyethane in view of overall properties, such as cost and handling ease. These solvents may be used alone or in combination. When the solvents are used in combination, the mixing ratio is not particularly limited.

A compound (5) having the S absolute configuration at *2 and the R absolute configuration at *1 or a compound (5) having the R absolute configuration at *2 and the S absolute configuration at *1 can be preferentially crystallized by using the combination of the sulfonic acid and the solvent described above.

When the acid is a hydrogen halide, such as hydrogen fluoride, hydrogen chloride, hydrogen bromide, or hydrogen iodide, in particular, hydrogen chloride or hydrogen bromide, the solvent is preferably an alcohol solvent such as methanol, ethanol, isopropanol, n-butanol, or ethylene glycol; or water. These solvents can be used alone or in combination. When alcohol solvents are used in combination, the mixing ratio is not particularly limited. When water is used in combination with alcohol solvents, the weight-based water/alcohol ratio is preferably 1 or less. Preferably, the solvent is ethanol or a mixture of ethanol and water.

By combining the hydrogen halide and the solvent described above, a compound (5) having the R absolute configuration at *2 and the R absolute configuration at *1 or a compound (5) having the S absolute configuration at *2 or the S absolute configuration at *1 can be preferentially crystallized.

The quantity of the solvent is preferably selected so that the fluidity of the product is sufficient upon completion of the process of crystallizing the compound (5). For example, the weight of the solvent is preferably up to 50 times and more preferably about 1 to 30 times the weight of the compound (3).

During the reaction and crystallization, the method of adding the compound (3), the acid, and the solvent, and the order of adding them are not particularly limited. Preferably, the acid is added to a solution of the compound (3) in the solvent, or the compound (3) is added to a solution of the acid in the solvent. The crystallization is preferably gradually performed while adding the reagent. It is possible to employ another method including the steps of producing a salt from the compound (3) and the acid in a solvent that does not allow crystallization, removing the solvent by distillation, for example, under heating at a reduced pressure, to obtain a diastereomer mixture of the compound (5), and conducting recrystallization while adding a solvent. Cooling crystallization, condensation crystallization, or a combination of these may be employed as the crystallization method. The condensation crystallization may be a method in which the solution containing the above-described solvent gradually replaces another solution containing a solvent other than the solvent described above. In the crystallization process, seed crystals may be added.

The reaction and crystallization in this step can be performed at about room temperature, or, if necessary, under heating or under cooling. For example, the temperature may be about 60° C. or less, and typically in the range of −30° C. to 50° C.

The compound (5) obtained as such is subjected to solid-liquid separation. If the mother liquor remains in the obtained crystals, thereby degrading the quality of the crystals, the crystals may be washed and dried, as necessary. The method for solid-liquid separation is not particularly limited. Examples thereof include pressure filtration, vacuum filtration, and centrifugal separation. For example, the crystals are preferably dried at about 60° C. or less under a reduced pressure, i.e., in vacuum, to avoid pyrolysis and melting.

The compound (5) obtained as above may be easily converted to an optically active α-substituted aminoketone represented by formula (4) by simply treating the obtained compound (5) with an alkaline aqueous solution, such as a sodium hydroxide aqueous solution, a potassium carbonate aqueous solution, or a sodium hydrogen carbonate aqueous solution.

A step of producing an optically active β-substituted amino alcohol represented by formula (6) or a salt thereof by stereoselectively reducing an optically active α-substituted aminoketone represented by formula (4) or an optically active α-substituted aminoketone salt represented by formula (5) will now be described.

Examples of the reductant used in this step include boron compounds such as lithium borohydride, sodium borohydride, potassium borohydride, zinc borohydride, tetrabutylammonium borohydride, tetrabutylammonium cyanoborohydride, lithium triethylborohydride, lithium tri-sec-butylborohydride, lithium triisoamylborohydride, sodium triethylborohydride, sodium tri-sec-butylborohydride, sodium triacetoxyborohydride, diborane, borane-dimethylsulfide complexes, borane-tetrahydrofuran complexes, borane-morpholine complexes, borane-triphenylphosphine complexes, catecholborane, and 9-borabicyclo[3,3,1]nonane; and hydride reductants of aluminum compounds and the like, such as lithium aluminum hydride, diisobutylaluminum hydride, and lithium tri-tert-butoxyaluminohydride. Preferably, the reductant is lithium borohydride, sodium borohydride, potassium borohydride, zinc borohydride, or tetrabutylammonium borohydride. Most preferably, the reductant is sodium borohydride.

Alternatively, a reductant of a hydrogen-transfer type may be used. Examples of such a reductant include aluminum triisopropoxide and aluminum isopropoxides prepared from isopropanol and aluminum compounds such as trimethylaluminum, diisobutylaluminum hydride, and triisobutylaluminum.

The molar quantity of the reductant used is preferably 0.25 to 5 times and more preferably 0.5 to 2 times that of the compound (4) or (5).

The reaction temperature is preferably −50° C. to 70° C. and more preferably −10° C. to 40° C. in view of reducing the reaction time and increasing the yield.

Examples of the solvent that may be used in the reaction include hydrocarbon solvents such as hexane, heptane, benzene, and toluene; ether solvents such as diethyl ether, tetrahydrofuran, 1,4-dioxane, methyl tert-butyl ether, and dimethoxyethane; ester solvents such as ethyl acetate, n-propyl acetate, and tert-butyl acetate; halogenated solvents such as methylene chloride, chloroform, and 1,1,1-trichloroethane; amide solvents such as dimethylformamide, dimethylacetamide, and N-methylpyrrolidone; nitrile solvents such as acetonitrile and propionitrile; sulfoxide solvents such as dimethylsulfoxide; phosphoric amide solvents such as hexamethylphosphoric triamide; alcohol solvents such as methanol, ethanol, isopropanol, n-butanol, and ethylene glycol; and water. These solvents may be used alone or in combination. When the solvents are used in combination, the mixing ratio is not particularly limited. More preferably, the solvent is ethanol or a mixture of ethanol and water.

The weight of the solvent used is preferably up to about 50 times and more preferably about 1 to 30 times that of the compound (4) or (5).

During the reaction, the method of adding the compound (4) or (5), the reductant, and the solvent, or the order of adding these is not particularly limited.

The stereoselectivity of this reaction is preferably the anti selectivity. In particular, an optically active β-substituted amino alcohol (6) having the S absolute configuration at *2 and the R absolute configuration at *3, or having the R absolute configuration at *2 and the S absolute configuration at *3 is preferred. An optically active β-substituted amino alcohol (6) having the S absolute configuration at *2, the R absolute configuration at *1, and R absolute configuration at *3; having the R absolute configuration at *2, the R absolute configuration at *1, and the S absolute configuration at *3; having the R absolute configuration at *2, the S absolute configuration at *1, and the S absolute configuration at *3; or having the S absolute configuration at *2, the S absolute configuration at *1, and the R absolute configuration at *3 is preferred.

After this reaction, a typical post-treatment may be performed to obtain the reaction product from the reaction solution. For example, upon completion of the reaction, the reaction solution may be neutralized by adding water, or if necessary, an aqueous acid such as aqueous hydrochloric acid, aqueous sulfuric acid, or aqueous acetic acid, followed by a typical extraction process using a typical extraction solvent, for example, ethyl acetate, diethyl ether, methylene chloride, toluene, or hexane. The reaction solvent and the extraction solvent are removed from the resulting extract by, for example, heating under a reduced pressure to obtain a target product. Although the product obtained as such already has a sufficiently high purity for subsequent steps, the purity of the product may be further increased by a typical purification method, such as column chromatography, fractional distillation, or crystallization, or by precipitating a salt with an acid in an appropriate solvent in order to further increase the yield in the subsequent step or the purity of the compound obtained in the subsequent step.

The step of synthesizing a β-amino alcohol represented by general formula (7) or a salt thereof by hydrogenolysis of an optically active β-substituted amino alcohol represented by general formula (6) or a salt thereof will now be described.

The hydrogenolysis reaction may be conducted by using hydrogen in the presence of a transition metal catalyst or through hydrogen transfer reaction using isopropanol, sec-butanol, formic acid, ammonium formate, triethylammonium formate, or the like, in the presence of a transition metal catalyst.

The transition metal catalyst is, for example, platinum, rhodium, palladium, nickel, ruthenium, iridium, or rhenium. Examples of the transition metal catalyst include metals, such as platinum, rhodium, palladium, nickel, ruthenium, iridium, and rhenium, alloys thereof, chlorides thereof, bromides thereof, iodides thereof, nitrates thereof, sulfates thereof, phosphates thereof, oxides thereof, sulfides thereof, borides thereof, hydroxides thereof, cyanide thereof, acetylacetonates thereof, acetates thereof, and trifluoroacetates thereof. Specific examples of the catalyst include platinum metal, platinum black, platinum(II) acetylacetonate, platinum(II) bis(benzonitrile)dichloride, platinum(II) bromide, platinum (IV) bromide, platinum(II) chloride, platinum(IV) chloride, platinum(II) cyanide, platinum(II) iodide, a platinum iridium alloy, platinum(IV) oxide, platinum(IV) oxide hydrate, a platinum rhodium alloy, a platinum palladium alloy, platinum (IV) sulfide, rhodium metal, rhodium black, rhodium(II) acetate, rhodium(II) acetylacetonate, rhodium(II) bromide hydrate, rhodium(III) chloride, rhodium(III) chloride hydrate, rhodium(II) hexafluorobutanate, rhodium(II) hexanoate, rhodium(III) iodide hydrate, rhodium(III) nitrate, rhodium(III) oxide, rhodium(III) oxide hydrate, rhodium(III) phosphate, rhodium(III) sulfate, rhodium(II) trifluoroacetate, palladium metal, palladium black, palladium(II) acetate, palladium(II) acetylacetonate, palladium(II) bis(benzonitrile) dichloride, palladium(II) bromide, palladium(II) chloride, palladium(II) cyanide, palladium(II) hydroxide, palladium (II) iodide, palladium(II) nitrate, palladium(II) nitrate hydrate, palladium(II) oxide, palladium(II) oxide hydrate, palladium(II) propionate, palladium(II) sulfate, palladium (II) sulfide, palladium(II) trifluoroacetate, nickel metal, Raney nickel, nickel boride, nickel(II) oxide, ruthenium metal, ruthenium black, ruthenium(III) acetylacetonate, ruthenium(III) bromide, ruthenium(III) bromide hydrate, ruthenium(III) chloride, ruthenium(III) chloride hydrate, ruthenium(III) iodide, nitrosylruthenium(III) chloride hydrate, nitrosylruthenium(III) nitrate, ruthenium(IV) oxide, ruthenium(IV) oxide hydrate, iridium metal, iridium(III) acetylacetonate, iridium(III) bromide hydrate, iridium(III) chloride, iridium(III) chloride hydrochloride, iridium(IV) chloride hydrate, iridium(IV) oxide, iridium(IV) oxide hydrate, rhenium metal, rhenium(III) chloride, rhenium(V) chloride, rhenium(IV) fluoride, rhenium(IV) oxide, rhenium (VI) oxide, rhenium(VII) oxide, and rhenium(VII) sulfide.

These catalysts are preferably supported by powdery carriers in view of catalytic activity, reproducibility, storage stability, handling ability, and recycling. Examples of the powdery carriers include carbon, alumina, silica-alumina, silica, barium carbonate, barium sulfate, calcium carbonate, titanium oxide, zirconium oxide, zeolite, and asbestos. Preferably, the catalyst is a metal, such as platinum, rhodium, or palladium, a sulfide thereof, or a hydroxide thereof supported by any of these powdery carriers.

In particular, examples of the combination of the catalyst and powdery carrier include platinum-carbon, platinum(II) sulfide-carbon, platinum-alumina, platinum-silica-alumina, platinum-silica, platinum-barium carbonate, platinum-barium sulfate, platinum-calcium carbonate, platinum-titanium oxide, platinum-zirconium oxide, platinum-zeolite, platinum-asbestos, platinum rhodium alloy-carbon, platinum palladium alloy-carbon, rhodium-carbon, rhodium-alumina, rhodium-silica, rhodium-calcium carbonate, palladium-carbon, palladium (II) hydroxide-carbon, palladium(II) sulfide-carbon, palladium-alumina, palladium-silica-alumina, palladium-silica, palladium-barium carbonate, palladium-barium sulfate, palladium-calcium carbonate, palladium-titanium oxide, palladium-zirconium oxide, palladium-zeolite, palladium-asbestos, ruthenium-carbon, ruthenium-alumina, ruthenium-silica, ruthenium-calcium carbonate, iridium-carbon, iridium-alumina, iridium-silica, and iridium-calcium carbonate. Preferably, the catalyst is palladium-carbon, rhodium-carbon, platinum-carbon, platinum palladium alloy-carbon, or palladium(II) hydroxide-carbon. More preferably, the catalyst is palladium-carbon or palladium(II) hydroxide-carbon. These transition metal catalysts may be used alone or in combination. The molar quantity of the transition metal catalyst used is preferably less than or equal to, more preferably up to 0.5 times, and most preferably up to 0.2 times the molar quantity of the compound (6).

The reaction temperature during this reaction is preferably −20° C. to 100° C. and more preferably 0° C. to 70° C. in view of reducing the reaction time and increasing the yield. The hydrogen pressure in this reaction is preferably 50 atm or less and more preferably 1 to 10 atm in view of reducing the reaction time and increasing the yield.

Examples of the reaction solvent that can be used in this reaction include water; alcohol solvents such as methanol, ethanol, isopropanol, and n-butanol; hydrocarbon solvents such as hexane, heptane, benzene, and toluene; ether solvents such as diethyl ether, tetrahydrofuran, 1,4-dioxane, methyl tert-butyl ether, and dimethoxyethane; ester solvents such as ethyl acetate, n-propyl acetate, and tert-butyl acetate; ketone solvents such as acetone and methyl ethyl ketone; halogenated solvents such as methylene chloride, chloroform, and 1,1,1,-trichloroethane; amide solvents such as dimethylformamide, acetamide, formamide, and N-methylpyrrolidone; nitrile solvents such as acetonitrile and propionitrile; sulfoxide solvents such as dimethylsulfoxide; and phosphoric amide solvents such as hexamethylphosphoric triamide. These organic solvents may be used alone or in combination. When the solvents are used in combination, the mixing ratio is not particularly limited.

The reaction solvent is preferably water, methanol, ethanol, toluene, ethyl acetate, acetone, methylene chloride, methyl tert-butyl ether, tetrahydrofuran, dimethylformamide or the like. More preferably, the reaction solvent is water, methanol, ethanol, tetrahydrofuran, or the like.

The method of adding the compound (6), the transition metal catalyst, and the solvent and the order of adding these are not particularly limited. When hydrogen is used, the solution containing these may be evacuated before hydrogen charging.

After this reaction, a typical post-treatment may be performed to obtain a reaction product from the reaction solution. For example, the reaction solution after the termination of the reaction may be mixed with water, followed by an extraction process that uses a typical extraction solvent, e.g., ethyl acetate, diethyl ether, methylene chloride, toluene, or hexane. The resulting extract is heated under a reduced pressure to distill off the reaction solvent and the extraction solvent, thereby obtaining a target substance. When a transition metal catalyst insoluble in the reaction solvent is used, the transition metal catalyst may be filtered off by a process such as vacuum filtration, pressure filtration, or centrifugation. The filtrate is then heated under a reduced pressure to distill off the reaction solvent to obtain a target substance. Although the obtained substance has a sufficiently high purity, the purity of the product may be further increased by a typical purification method, such as column chromatography, fractional distillation, or crystallization, or by precipitating a salt with an acid in an appropriate solvent.

The compound (7) obtained as such retains the configuration of the compound (6). Preferably, the compound (7) has the S absolute configuration at *2 and the R absolute configuration at *3 or has the R absolute configuration at *2 and the S absolute configuration at *3.

A step of synthesizing an optically active β-amino alcohol represented by formula (9) or a salt thereof:

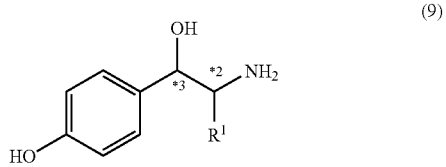

(9)

(wherein $R^1$, *2, and *3 are the same as above) by performing hydrogenolysis of an optically active β-substituted amino alcohol represented by formula (8) or a salt thereof:

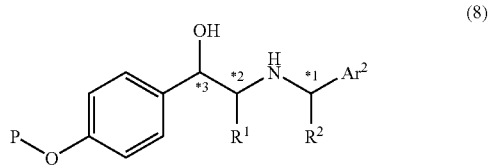

(8)

(wherein $Ar^2$, $R^1$, $R^2$, P, *1, *2, and *3 are the same as above), wherein deprotection of the hydroxyl group may be performed before the hydrogenolysis, if necessary, will now be described.

In general, the benzyl-type protecting group can be removed by hydrogenation in the presence of a transition metal catalyst. Thus, the hydrogenolysis may be conducted continuously after the deprotection without performing a post-treatment.

In this step, the type and amount of the usable transition metal catalyst, the reaction temperature, the hydrogen pressure, the usable solvent, and the post-treatment are the same as those described in detail in the step of preparing the optically active β-amino alcohol represented by formula (7) or a salt thereof synthesized by hydrogenolysis of the optically active β-substituted amino alcohol represented by formula (6) or a salt thereof.

Removal of an aroyl-type protecting group may be conducted by solvolysis or hydrolysis according to any one of the following methods: a method in which the protecting group is interacted with a base, such as lithium hydroxide, sodium hydroxide, potassium hydroxide, sodium methoxide, sodium ethoxide, ammonia, methylamine, ethylamine, or n-butylamine, in water, an alcohol solvent, such as methanol, ethanol, or isopropanol, or a mixed solvent containing water and an alcohol solvent such as methanol, ethanol, or isopropanol; and a method in which the protecting group is interacted with an acid, such as hydrogen chloride (hydrochloric acid), hydrogen bromide (hydrobromic acid), sulfuric acid, nitric acid, methanesulfonic acid, p-toluenesulfonic acid, or a trifluoroacetic acid, in water, an alcohol solvent, such as methanol, ethanol, or isopropanol, or a mixed solvent containing water and an alcohol solvent such as methanol, ethanol, or isopropanol.

The molar quantity of the base used is preferably 1 to 50 times and more preferably 1 to 10 times the molar quantity of the compound (8) described above. The molar quantity of the acid used is preferably up to 20 times and more preferably less than or equal to that of the compound (8) described above.

The reaction temperature in this step is preferably −30° C. to 100° C. and more preferably 0° C. to 50° C. in view of reducing the reaction time and increasing the yield.

During the reaction, the method of adding the compound (8), the base or the acid, and the solvent and the order of adding these are not particularly limited.

Removal of a sulfonyl-type protecting group may be conducted by interaction with a base, such as lithium hydroxide, sodium hydroxide, potassium hydroxide, sodium methoxide, sodium ethoxide, ammonia, methylamine, ethylamine, or n-butylamine, in water, an alcohol solvent such as methanol, ethanol, or isopropanol, or a mixed solvent containing water and an alcohol solvent such as methanol, ethanol, or isopropanol.

The molar quantity of the base used is preferably 1 to 50 times and more preferably 1 to 10 times the molar quantity of the compound (8).

The reaction temperature in this step is preferably 0° C. to 100° C. and more preferably 20° C. to 70° C. in view of reducing the reaction time and increasing the yield.

During the reaction, the method of adding the compound (8), the base, and the solvent and the order of adding these are not particularly limited.

The optically active β-substituted amino alcohol represented by formula (8) with P representing a hydrogen atom, or a salt thereof deprotected as above can be converted to an optically active β-amino alcohol represented by formula (9) or a salt thereof by hydrogenation in the presence of a transition metal catalyst. In this step, the type and the amount of the usable transition metal catalyst, the reaction temperature, the hydrogen pressure, the usable solvent, the post-treatment, and the like are the same as those described in detail in the step of preparing the optically active β-amino alcohol represented by formula (7) or a salt thereof synthesized by hydrogenolysis of the optically active β-substituted amino alcohol represented by formula (6) or a salt thereof described in the previous sections.

The step of producing an optically active β-amino alcohol represented by formula (7) or a salt thereof by stereoselective reduction of an optically active α-substituted aminoketone represented by formula (4) or an optically active α-substituted aminoketone salt represented by formula (5) while simultaneously performing hydrogenolysis will now be described.

The stereoselective reduction and the hydrogenolysis in this step may be performed using hydrogen in the presence of a transition metal catalyst. In this step, the type and the amount of the usable transition metal catalyst, the reaction temperature, the hydrogen pressure, the usable solvent, the post-treatment, and the like are the same as those described in detail in the step of preparing the optically active β-amino alcohol represented by formula (7) or a salt thereof synthesized by hydrogenolysis of the optically active β-substituted amino alcohol represented by formula (6) or a salt thereof described in the previous sections.

In this reaction, the anti isomer is preferably selectively reacted. In other words, the optically active β-amino alcohol represented by formula (7) preferably has the S absolute configuration at *2 and the R absolute configuration at *3, or has the R absolute configuration at *2 and the S absolute configuration at *3.

A step of producing an optically active β-amino alcohol represented by formula (9) or a salt thereof by simultaneously carrying out stereoselective reduction and hydrogenolysis of an optically active α-substituted aminoketone represented by formula (4) or an optically active α-substituted aminoketone salt represented by formula (5) having $Ar^1$ representing a p-hydroxyphenyl group or a hydroxyl-protected p-hydroxyphenyl group represented by formula (10) will now be described. If necessary, deprotection may be performed before the stereoselective reduction and hydrogenolysis.

In this step, the method of deprotecting the hydroxyl group is the same as that regarding the compound (8) described above.

The resulting optically active α-substituted aminoketone represented by formula (4) or optically active α-substituted aminoketone salt represented by formula (5) having a p-hydroxyphenyl group as $Ar^1$ is hydrogenated in the presence of a transition metal catalyst to produce an optically active β-amino alcohol represented by formula (9) or a salt thereof.

In this step, the type and amount of the usable transition metal catalyst, the reaction temperature, the hydrogen pressure, the usable solvent, the post-treatment, and the like are the same as those described in detail in the step of preparing the optically active β-amino alcohol represented by formula (7) or a salt thereof by hydrogenolysis of the optically active β-substituted amino alcohol represented by formula (6) or a salt thereof described in the previous sections.

The resulting optically active β-amino alcohol represented by formula (9) or a salt thereof with an optically inactive acid may be isolated as crystals by precipitation from an alcohol solvent, thereby removing impurities to the mother liquor.

Preferable examples of the salt with the optically inactive acid include inorganic salts such as hydrochloride, hydrobromide, nitrate, sulfate, perchlorate, phosphate, and borate; sulfonates such as methanesulfonate, benzenesulfonate, p-toluenesulfonate, and trifluoromethanesulfonate; and carboxylates such as acetate, propionate, oxalate, benzoate, p-nitrobenzoate, and malonate. More preferable examples are hydrochloride, hydrobromide, and methanesulfonate.

Examples of the alcohol solvent include methanol, ethanol, isopropanol, n-butanol, sec-butanol, tert-butanol, cyclohexanol, and ethylene glycol. Preferably, the alcohol solvent is methanol, ethanol, or isopropanol. These alcohol solvents may be used alone or in combination. When the solvents are used in combination, the mixing ratio is not particularly limited.

The alcohol solvent is preferably used in an amount that can render sufficient fluidity to the product upon completion of the process for crystallizing the compound (9). For example, the weight of the alcohol solvent is about 50 times or less or more preferably about 1 to 30 times the weight of the compound (9).

Examples of the impurities that can be removed in the present invention include byproduct impurities (structural analogs) produced during the synthesis of the compound (9) and, of the four stereoisomers of the compound (9), those not having the target configuration, e.g., an enantiomer, a diastereomer, and a diastereomer of an enantiomer. The present invention is particularly advantageous in removing diastereomers and enantiomers, which are, in general, difficult to remove.

When the target compound is a compound represented by formula (9) having the S absolute configuration at *2 and the R absolute configuration at *3, the impurity is either a compound (diastereomer) having the S absolute configuration at *2 and the S absolute configuration at *3 or a compound (enantiomer) having the R absolute configuration at *2 and the S absolute configuration at *3. When the target compound is a compound represented by formula (9) having the R absolute configuration at *2 and the S absolute configuration at *3, the impurity is either a compound (diastereomer) having the R absolute configuration at *2 and the R absolute configuration at *3 or a compound (enantiomer) having the S absolute configuration at *2 and the R absolute configuration at *3.

In this invention, an auxiliary solvent may be used to improve at least one of the yield of the compound represented by formula (9), the process concentration, the liquid properties, and the physical properties of the crystals obtained.

Examples of the auxiliary solvent include, but are not limited to, water; ester solvents such as ethyl acetate, n-propyl acetate, and tert-butyl acetate; ether solvents such as diethyl ether, tetrahydrofuran, 1,4-dioxane, methyl tert-butyl ether, dimethoxyethane, and diisopropyl ether; ketone solvents such as acetone and methyl ethyl ketone; halogenated solvents such as methylene chloride, chloroform, and 1,1,1-trichloroethane; hydrocarbon solvents such as hexane, heptane, benzene, and toluene; and nitrile solvents such as acetonitrile and propionitrile. These auxiliary solvents may be used alone or in combination. When the solvents are used in combination, the mixing ratio is not particularly limited. The solvent is preferably ethyl acetate, diethyl ether, tetrahydrofuran, methyl tert-butyl ether, diisopropylether, acetone, methylene chloride, chloroform, hexane, toluene, or acetonitrile. More preferably, the solvent is ethyl acetate, toluene, or methylene chloride. The appropriate amount of the auxiliary solvent can be determined by a simple experiment. For example, the amount of the auxiliary solvent is preferably such that the volume ratio of the auxiliary solvent to the alcohol solvent upon completion of the crystallization process is 0.1 or more and more preferably 1 or more.

Cooling crystallization, condensation crystallization, or the like, or a combination of these may be employed as the method for crystallizing the compound (9). The condensation crystallization may be a method in which the solution containing the above-described alcohol solvent gradually replaces another solution containing a solvent other than the alcohol solvent described above. Preferably, the auxiliary solvent is added to a solution of the compound (9) in the alcohol solvent described above. In the crystallization process, seed crystals may be added.

In this step, purification and isolation can be performed at around room temperature, or, if necessary, under heating or under cooling. For example, the isolation is performed at about 60° C. or lower and typically in the range of −30° C. to 50° C.

The compound (9) obtained as such is subjected to solid-liquid separation. If the mother liquor remains in the obtained crystals, thereby degrading the quality of the crystals, the crystals may be washed and dried, as necessary. The method for solid-liquid separation is not particularly limited. Examples thereof include pressure filtration, vacuum filtration, and centrifugal separation. The crystals are preferably dried at about 60° C. or less under a reduced pressure, i.e., in vacuum, to avoid pyrolysis and melting.

BEST MODE FOR CARRYING OUT THE INVENTION

The present invention will now be described by way of Examples. The scope of the preset invention is by no means limited to these examples.

EXAMPLE OF SYNTHESIZING α-SUBSTITUTED KETONE (1)

Reference Example 1

1-[4-(benzyloxy)phenyl]-2-bromo-1-propanone

To 100 mL of a tetrahydrofuran solution of 24.00 g (100 mmol) of 4-benzyloxypropiophenone, a hexane solution (20 mL) of 23.973 g (1.5 equivalents) of bromine was gradually added at 20° C., followed by 1 hour of stirring. To the resulting solution, 50 mL of a saturated sodium hydrogen carbonate solution and 100 mL of ethyl acetate were added to conduct extraction. The organic layer was washed with 30 mL of a 20 wt % sodium thiosulfate aqueous solution, dried over anhydrous magnesium sulfate, and subjected to distillation under a reduced pressure to remove the solvents. A colorless, oily substance was obtained as a result. To this substance, 200 mL of hexane was added to precipitate crystals. White crystals (31.12 g; isolation yield: 95%) of 1-[4-(benzyloxy)phenyl]-2-bromo-1-propanone were obtained as a result.

EXAMPLE OF SYNTHESIZING OPTICALLY ACTIVE α-SUBSTITUTED AMINOKETONE (4) FROM α-SUBSTITUTED KETONE (1)

EXAMPLE 1

Synthesis of (2R)-1-[4-(benzyloxy)phenyl]-2-[((1S)-phenylethyl)amino]-1-propanone To an acetonitrile solution (20 mL) of 3.19 g (10 mmol) of 1-[4-(benzyloxy)phenyl]-2-bromo-1-propanone synthesized in REFERENCE EXAMPLE 1, 2.662 g (22 mmol) of (S)-1-phenethylamine was added, and the mixture was stirred for 4 hours at 40° C. After the solvent was distilled off under a reduced pressure, 30 mL of ethyl acetate and 20 mL of water were added to conduct extraction. The extract was washed with 20 mL of water, dried over anhydrous magnesium sulfate, and subjected to distillation under a reduced pressure to remove the solvents. An yellow, oily diastereomer mixture of 1-[4-(benzyloxy)phenyl]-2-[((1S)-phenylethyl)amino]-1-propanone was obtained as a result (reaction yield: 80%). The diastereomer ratio of this mixture was determined by high-performance liquid chromatography (column: YMC ODS-A A-303 4.6×50 mm, eluent: acetonitrile/1 mM phosphoric acid buffer solution (pH=2.5)=1/1, flow: 0.5 mL/min, column temperature: 40° C., detector: UV 210 nm, retention time: (2R)-isomer=8.3 min., (2S)-isomer=8.4 min). The ratio, (2R)-isomer/(2S)-isomer, was 1/1. The mixture was then purified by silica gel column chromatography (developed with ethyl acetate/hexane=1/4) to obtain a light yellow solid of (2R)-1-[4-(benzyloxy)phenyl]-2-[((1S)-phenylethyl)amino]-1-propanone (242.6 mg, isolation yield: 6%, (2R)-isomer/(2S)-isomer=93/7 (86% d.e.).

$^1$H-NMR (CDCl$_3$, 400 MHz/ppm): δ 1.29 (3H, d), 1.38 (3H, d), 2.1-2.6 (1H, brs), 3.87 (1H, q), 4.24 (1H, q), 5.11 (2H, s), 6.97 (2H, d), 7.2-7.5 (10H, m), 7.80 (2H, d)

EXAMPLE OF SYNTHESIZING OPTICALLY ACTIVE α-SUBSTITUTED AMINOKETONE SALT (5) FROM α-SUBSTITUTED KETONE (1)

EXAMPLE 2

Synthesis of (2R)-1-[4-(benzyloxy)phenyl]-2-[((1S)-phenylethyl)amino]-1-propanone methanesulfonate To an acetonitrile solution (20 mL) of 2.797 g (8.77 mmol) of 1-[4-(benzyloxy)phenyl]-2-bromo-1-propanone synthesized in REFERENCE EXAMPLE 1 and 1.775 g (2 equivalents) of triethylamine, 1.273 g (1.2 equivalents) of (S)-phenethylamine was added. The mixture was stirred for 16 hours at 40° C. To the mixture, 20 mL of water was added, and the solvents were distilled off under a reduced pressure. Extraction was then conducted while adding 30 mL of ethyl acetate.

The organic layer was washed with 10 mL of a saturated sodium hydrogen carbonate solution, dried over anhydrous magnesium sulfate, and subjected to distillation under a reduced pressure to remove the solvents. An yellow, oily diastereomer mixture of 1-[4-(benzyloxy)phenyl]-2-[((1S)-phenylethyl)amino]-1-propanone was obtained as a result (reaction yield: 79%). Next, the mixture was mixed with 30 mL of ethyl acetate to prepare a homogeneous solution. To the homogeneous solution, 1.01 g of methanesulfonic acid was added, and the mixture was stirred at 15° C. for 30 minutes to precipitate crystals. The crystals were filtered off under a reduced pressure. White crystals of (2R)-1-[4-(benzyloxy)phenyl]-2-[((1S)-phenylethyl)amino]-1-propanone methanesulfonate (855.1 mg, isolation yield: 20%) were obtained as a result. The diastereomer ratio thereof was determined as in EXAMPLE 1. The ratio, (2R)-isomer/(2S)-isomer, was 100/0 (100% d.e.).

$^1$H-NMR (CDCl$_3$, 400 MHz/ppm): δ 1.70 (3H, d), 1.89 (3H, d), 2.82 (3H, s), 4.54 (1H, brs), 4.85 (1H, brs), 5.13 (2H, s), 6.96 (2H, d), 7.2-7.3 (3H, m), 7.3-7.5 (5H, m), 7.69 (2H, d), 7.71 (2H, d), 8.06 (1H, brs), 10.17 (1H, brs)

EXAMPLE OF SYNTHESIZING OPTICALLY ACTIVE α-SUBSTITUTED AMINOKETONE SALT (5) FROM α-SUBSTITUTED KETONE (1)

EXAMPLE 3

Synthesis of (2S)-1-[4-(benzyloxy)phenyl]-2-[((1R)-phenylethyl)amino]-1-propanone methanesulfonate To an acetonitrile solution (100 mL) of 31.12 g (95.4 mmol) of 1-[4-(benzyloxy)phenyl]-2-bromo-1-propanone synthesized in REFERENCE EXAMPLE 1 and 19.31 g (2 equivalents) of triethylamine, 13.852 g (1.2 equivalents) of (R)-phenethylamine was added, and the resulting solution was stirred for 16 hours at 40° C. After 50 mL of water was added to the solution, the solvent was distilled off under a reduced pressure, and 100 mL of ethyl acetate was added to conduct extraction. The organic layer was washed with 50 mL of a saturated sodium hydrogen carbonate solution, dried over anhydrous magnesium sulfate, and subjected to distillation under a reduced pressure to remove the solvent. An yellow, oily diastereomer mixture of 1-[4-(benzyloxy)phenyl]-2-[((1R)-phenylethyl)amino]-1-propanone was obtained as a result (reaction yield: 85%). To this substance, 100 mL of ethyl acetate was added to prepare a homogeneous solution. To the homogenous solution, 7.785 g of methanesulfonic acid was added, the mixture was stirred for 1 hour at 15° C. to precipitate crystals. The crystals were filtered off under a reduced pressure. White crystals of (2S)-1-[4-(benzyloxy)phenyl]-2-[((1R)-phenylethyl)amino]-1-propanone methanesulfonate were obtained as a result (18.84 g, isolation yield 43%). The diastereomer ratio thereof was determined by high-performance liquid chromatography (column: Daicel Chiralpak AD 4.6×250 mm, eluent: hexane/isopropanol=10/1, flow: 0.5 mL/min, column temperature: 35° C., detector: UV 210 nm, retention time: (2S)-isomer=16.1 min., (2R)-isomer=12.2 min). The ratio, (2S)-isomer/(2R)-isomer, was 96.5/3.5 (92.0% d.e.).

EXAMPLE OF SYNTHESIZING DIASTEREOMER (3) OF OPTICALLY ACTIVE α-SUBSTITUTED AMINOKETONE FROM α-SUBSTITUTED KETONE (1)

EXAMPLE 4

Synthesis of diastereomer mixture of 1-[4-(benzyloxy)phenyl]-2-[((1R)-phenylethyl)amino]-1-propanone To an acetonitrile solution (100 mL) of 25.00 g (78.3 mmol) of 1-[4-(benzyloxy)phenyl]-2-bromo-1-propanone synthesized in REFERENCE EXAMPLE 1 and 15.85 g (2 equivalents) of triethylamine, 11.389 g (1.2 equivalents) of (R)-phenethylamine was added, and the mixture was stirred for 16 hours at 40° C. After addition of 50 mL of water, the solvent was distilled off under a reduced pressure, and 100 mL of ethyl acetate was added to conduct extraction. The organic layer was washed with 50 mL of a saturated sodium hydrogen carbonate solution, dried over anhydrous magnesium sulfate, and subjected to distillation under a reduced pressure to remove the solvent. An yellow, oily diastereomer mixture of 1-[4-(benzyloxy)phenyl]-2-[((1R)-phenylethyl)amino]-1-propanone (30.2238 g, 86.8 percent by weight, reaction yield: 93%) was obtained as a result.

EXAMPLE (SYNTHETIC EXAMPLE) OF ISOLATING AN OPTICALLY ACTIVE α-SUBSTITUTED AMINOKETONE SALT (5) BY ADDING A SOLVENT TO A DIASTEREOMER MIXTURE (3) OF OPTICALLY ACTIVE α-SUBSTITUTED AMINOKETONE TO PREPARE A HOMOGENEOUS SOLUTION, PRODUCING A SALT BY ADDING AN ACID, AND PREFERENTIALLY CRYSTALLIZING ONE DIASTEREOMER FROM THE SOLUTION

EXAMPLE 5

Synthesis of (2S)-1-[4-(benzyloxy)phenyl]-2-[((1R)-phenylethyl)amino]-1-propanone methanesulfonate A homogeneous solution was prepared by adding 10 mL of diethyl ether and 2 mL of methanol to 2.070 g (5 mmol) of the diastereomer mixture of 1-[4-(benzyloxy)phenyl]-2-[((1R)-phenylethyl)amino]-1-propanone prepared in EXAMPLE 4. To the homogeneous solution, 480.5 mg (1 equivalent) of methanesulfonic acid was added, and the mixture was stirred for 1 hour at 15° C. to precipitate crystals. The crystals were filtered off under a reduced pressure. White crystals of (2S)-1-[4-(benzyloxy)phenyl]-2-[((1R)-phenylethyl)amino]-1-propanone methanesulfonate were obtained as a result (725.9 mg, isolation yield 31%). The diastereomer ratio thereof was determined as in EXAMPLE 3. The ratio, (2S)-isomer/(2R)-isomer, was 99.0/1.0 (98.0% d.e.).

EXAMPLE (SYNTHETIC EXAMPLE) OF ISOLATING AN OPTICALLY ACTIVE α-SUBSTITUTED AMINOKETONE SALT (5) BY ADDING A SOLVENT TO A DIASTEREOMER MIXTURE (3) OF OPTICALLY ACTIVE α-SUBSTITUTED AMINOKETONE TO PREPARE A HOMOGENEOUS SOLUTION, PRODUCING A SALT BY ADDING AN ACID, AND PREDERENTIALLY CRYSTALLIZING ONE DIASTEREOMER FROM THE SOLUTION

EXAMPLE 6

Synthesis of (2S)-1-[4-(benzyloxy)phenyl]-2-[((1R)-phenylethyl)amino]-1-propanone methanesulfonate A homogeneous solution was prepared by adding 10 mL of isopropyl acetate to 2.070 g (5 mmol) of the diastereomer mixture of 1-[4-(benzyloxy)phenyl]-2-[((1R)-phenylethyl)amino]-1-propanone prepared in EXAMPLE 4. To the homogeneous solution, 480.5 mg (1 equivalent) of methanesulfonic acid was added, and the mixture was stirred for 1 hour at 15° C. to precipitate crystals. The crystals were filtered off under a reduced pressure. White crystals of (2S)-1-[4-(benzyloxy)phenyl]-2-[((1R)-phenylethyl)amino]-1-propanone methanesulfonate were obtained as a result (1453.6 mg, isolation yield: 60%). The diastereomer ratio thereof was determined as in EXAMPLE 3. The ratio, (2S)-isomer/(2R)-isomer, was 88.4/11.6 (76.8% d.e.).

EXAMPLE (SYNTHETIC EXAMPLE) OF ISOLATING AN OPTICALLY ACTIVE α-SUBSTITUTED AMINOKETONE SALT (5) BY ADDING A SOLVENT TO A DIASTEREOMER MIXTURE (3) OF OPTICALLY ACTIVE α-SUBSTITUTED AMINOKETONE TO PREPARE A HOMOGENEOUS SOLUTION, PRODUCING A SALY BY ADDING AN ACID, AND PREFERENTIALLY CRYSTALLIZING ONE DIASTEREOMER FROM THE SOLUTION

EXAMPLE 7

Synthesis of (2S)-1-[4-(benzyloxy)phenyl]-2-[((1R)-phenylethyl)amino]-1-propanone methanesulfonate A homogeneous solution was prepared by adding 5 mL of methylene chloride and 10 mL of toluene to 2.070 g (5 mmol) of the diastereomer mixture of 1-[4-(benzyloxy)phenyl]-2-[((1R)-phenylethyl)amino]-1-propanone prepared in EXAMPLE 4. To the homogeneous solution, 480.5 mg (1 equivalent) of methanesulfonic acid was added, and the mixture was stirred for 1 hour at 15° C. to precipitate crystals. The crystals were filtered off under a reduced pressure. White crystals of (2S)-1-[4-(benzyloxy)phenyl]-2-[((1R)-phenylethyl)amino]-1-propanone methanesulfonate were obtained as a result (925.3 mg, isolation yield: 37%). The diastereomer ratio thereof was determined as in EXAMPLE 3. The ratio, (2S)-isomer/(2R)-isomer, was 99.8/0.2 (99.6% d.e.).

EXAMPLE (SYNTHETIC EXAMPLE) OF ISOLATING AN OPTICALLY ACTIVE α-SUBSTITUTED AMINOKETONE SALT (5) BY ADDING A SOLVENT TO A DIASTEREOMER MIXTURE (3) OF OPTICALLY ACTIVE α-SUBSTITUTED AMINOKETONE TO PREPARE A HOMOGENEOUS SOLUTION, PRODUCING A SALT BY ADDING AN ACID, AND PREFERENTIALLY CRYSTALLIZING ONE DIASTEREOMER FROM THE SOLUTION

EXAMPLE 8

Synthesis of (2S)-1-[4-(benzyloxy)phenyl]-2-[((1R)-phenylethyl)amino]-1-propanone methanesulfonate A homogeneous solution was prepared by adding 5 mL of acetonitrile and 10 mL of toluene to 2.070 g (5 mmol) of the diastereomer mixture of 1-[4-(benzyloxy)phenyl]-2-[((1R)-phenylethyl)amino]-1-propanone prepared in EXAMPLE 4. To the homogeneous solution, 480.5 mg (1 equivalent) of methanesulfonic acid was added, and the mixture was stirred for 1 hour at 15° C. to precipitate crystals. The crystals were filtered off under a reduced pressure. White crystals of (2S)-1-[4-(benzyloxy)phenyl]-2-[((1R)-phenylethyl)amino]-1-propanone methanesulfonate were obtained as a result (822.3 mg, isolation yield: 34%). The diastereomer ratio thereof was determined as in EXAMPLE 3. The ratio, (2S)-isomer/(2R)-isomer, was 98.6/1.4 (97.2% d.e.).

EXAMPLE (SYNTHETIC EXAMPLE) OF ISOLATING AN OPTICALLY ACTIVE α-SUBSTITUTED AMINOKETONE SALT (5) BY ADDING A SOLVENT TO A DIASTEREOMER MIXTURE (3) OF OPTICALLY ACTIVE α-SUBSTITUTED AMINOKETONE TO PREPARE A HOMOGENEOUS SOLUTION, PRODUCING A SALT BY ADDING AN ACID, AND PREFERENTIALLY CRYSTALLIZING ONE DIASTEREOMER FROM THE SOLUTION

EXAMPLE 9

Synthesis of (2S)-1-[4-(benzyloxy)phenyl]-2-[((1R)-phenylethyl)amino]-1-propanone methanesulfonate A homogeneous solution was prepared by adding 5 mL of ethanol and 10 mL of hexane to 2.070 g (5 mmol) of the diastereomer mixture of 1-[4-(benzyloxy)phenyl]-2-[((1R)-phenylethyl)amino]-1-propanone prepared in EXAMPLE 4. To the homogeneous solution, 480.5 mg (1 equivalent) of methanesulfonic acid was added, and the mixture was stirred for 1 hour at 15° C. to precipitate crystals. The crystals were filtered off under a reduced pressure. White crystals of (2S)-1-[4-(benzyloxy)phenyl]-2-[((1R)-phenylethyl)amino]-1-propanone methanesulfonate were obtained as a result (774.7 mg, isolation yield: 33%). The diastereomer ratio thereof was determined as in EXAMPLE 3. The ratio, (2S)-isomer/(2R)-isomer, was 98.4/1.6 (96.8% d.e.).

EXAMPLE (SYNTHETIC EXAMPLE) OF ISOLATING AN OPTICALLY ACTIVE α-SUBSTITUTED AMINOKETONE SALT (5) BY ADDING A SOLVENT TO A DIASTEREOMER MIXTURE (3) OF OPTICALLY ACTIVE α-SUBSTITUTED AMINOKETONE TO PREPARE A HOMOGENEOUS SOLUTION, PRODUCING A SALT BY ADDING AN ACID, AND PREFERENTIALLY CRYSTALLIZING ONE DIASTEREOMER FROM THE SOLUTION

EXAMPLE 10

Synthesis of (2S)-1-[4-(benzyloxy)phenyl]-2-[((1R)-phenylethyl)amino]-1-propanone methanesulfonate A homogeneous solution was prepared by adding 10 mL of acetone to 2.070 g (5 mmol) of the diastereomer mixture of 1-[4-(benzyloxy)phenyl]-2-[((1R)-phenylethyl)amino]-1-propanone prepared in EXAMPLE 4. To the homogeneous solution, 480.5 mg (1 equivalent) of methanesulfonic acid was added, and the mixture was stirred for 1 hour at 15° C. to precipitate crystals. The crystals were filtered off under a reduced pressure. White crystals of (2S)-1-[4-(benzyloxy)phenyl]-2-[((1R)-phenylethyl)amino]-1-propanone methanesulfonate were obtained as a result (920.2 mg, isolation yield: 41%). The diastereomer ratio thereof was determined as in EXAMPLE 3. The ratio, (2S)-isomer/(2R)-isomer, was 99.8/0.2 (99.6% d.e.).

EXAMPLE (SYNTHETIC EXAMPLE) OF ISOLATING AN OPTICALLY ACTIVE α-SUBSTITUTED AMINOKETONE SALT (5) BY ADDING A SOLVENT TO A DIASTEREOMER MIXTURE (3) OF OPTICALLY ACTIVE α-SUBSTITUTED AMINOKETONE TO PREPARE A HOMOGENEOUS SOLUTION, PRODUCING A SALT BY ADDING AN ACID, AND PREFERENTIALLY CRYSTALLIZING ONE DIASTEREOMER FROM THE SOLUTION

EXAMPLE 11

Synthesis of (2S)-1-[4-(benzyloxy)phenyl]-2-[((1R)-phenylethyl)amino]-1-propanone methanesulfonate A homogeneous solution was prepared by adding 10 mL of dimethoxyethane to 2.070 g (5 mmol) of the diastereomer mixture of 1-[4-(benzyloxy)phenyl]-2-[((1R)-phenylethyl)amino]-1-propanone prepared in EXAMPLE 4. To the homogeneous solution, 480.5 mg (1 equivalent) of methanesulfonic acid was added, and the mixture was stirred for 1 hour at 15° C. to precipitate crystals. The crystals were filtered off under a reduced pressure. White crystals of (2S)-1-[4-(benzyloxy)phenyl]-2-[((1R)-phenylethyl)amino]-1-propanone methanesulfonate were obtained as a result (1,045.6 mg, isolation yield: 45%). The diastereomer ratio thereof was determined as in EXAMPLE 3. The ratio, (2S)/(2R), was 99.6/0.4 (99.2% d.e.).

EXAMPLE (SYNTHETIC EXAMPLE) OF ISOLATING AN OPTICALLY ACTIVE α-SUBSTITUTED AMINOKETONE SALT (5) BY ADDING A SOLVENT TO A DIASTEREOMER MIXTURE (3) OF OPTICALLY ACTIVE α-SUBSTITUTED AMINOKETONE TO PREPARE A HOMOGENEOUS SOLUTION, PRODUCING A SALT BY ADDING AN ACID, AND PREFERENTIALLY CRYSTALLIZING ONE DIASTEREOMER FROM THE SOLUTION

EXAMPLE 12

Synthesis of (2S)-1-[4-(benzyloxy)phenyl]-2-[((1R)-phenylethyl)amino]-1-propanone methanesulfonate A homogeneous solution was prepared by adding 5 mL of tetrahydrofuran and 5 mL of methyl tert-butyl ether to 2.070 g (5 mmol) of the diastereomer mixture of 1-[4-(benzyloxy)phenyl]-2-[((1R)-phenylethyl)amino]-1-propanone prepared in EXAMPLE 4. To the homogeneous solution, 480.5 mg (1 equivalent) of methanesulfonic acid was added, and the mixture was stirred for 1 hour at 15° C. to precipitate crystals. The crystals were filtered off under a reduced pressure. White crystals of (2S)-1-[4-(benzyloxy)phenyl]-2-[((1R)-phenylethyl)amino]-1-propanone methanesulfonate were obtained as a result (1,508.0 mg, isolation yield: 60%). The diastereomer ratio thereof was determined as in EXAMPLE 3. The ratio, (2S)-isomer/(2R)-isomer, was 96.5/3.5 (93.0% d.e.).

EXAMPLE (SYNTHETIC EXAMPLE) OF ISOLATING AN OPTICALLY ACTIVE α-SUBSTITUTED AMINOKETONE SALT (5) BY ADDING A SOLVENT TO A DIASTEREOMER MIXTURE (3) OF OPTICALLY ACTIVE α-SUBSTITUTED AMINOKETONE TO PREPARE A HOMOGENEOUS SOLUTION, PRODUCING A SALT BY ADDING AN ACID, AND PREFERENTIALLY CRYSTALLIZING ONE DIASTEREOMER FROM THE SOLUTION

EXAMPLE 13

Synthesis of (2S)-1-[4-(benzyloxy)phenyl]-2-[((1R)-phenylethyl)amino]-1-propanone methanesulfonate A homogeneous solution was prepared by adding 10 mL of isopropanol and 5 mL of tert-butyl acetate to 2.070 g (5 mmol) of the diastereomer mixture of 1-[4-(benzyloxy)phenyl]-2-[((1R)-phenylethyl)amino]-1-propanone prepared in EXAMPLE 4. To the homogeneous solution, 480.5 mg (1 equivalent) of methanesulfonic acid was added, and the mixture was stirred for 1 hour at 15° C. to precipitate crystals. The crystals were filtered off under a reduced pressure. White crystals of (2S)-1-[4-(benzyloxy)phenyl]-2-[((1R)-phenylethyl)amino]-1-propanone methanesulfonate were obtained as a result (821.6 mg, isolation yield: 35%). The diastereomer ratio thereof was determined as in EXAMPLE 3. The ratio, (2S)-isomer/(2R)-isomer, was 99.7/0.3 (99.4% d.e.).

EXAMPLE (SYNTHETIC EXAMPLE) OF ISOLATING AN OPTICALLY ACTIVE α-SUBSTITUTED AMINOKETONE SALT (5) BY ADDING A SOLVENT TO A DIASTEREOMER MIXTURE (3) OF OPTICALLY ACTIVE α-SUBSTITUTED AMINOKETONE TO PREPARE A HOMOGENEOUS SOLUTION, PRODUCING A SALT BY ADDING AN ACID, AND PREFERENTIALLY CRYSTALLIZING ONE DIASTEREOMER FROM THE SOLUTION

EXAMPLE 14

Synthesis of (2R)-1-[4-(benzyloxy)phenyl]-2-[((1R)-phenylethyl)amino]-1-propanone oxalate A homogeneous solution was prepared by adding 5 mL of ethyl acetate and 10 mL of tetrahydrofuran to 2.070 g (5 mmol) of the diastereomer mixture of 1-[4-(benzyloxy)phenyl]-2-[((1R)-phenylethyl)amino]-1-propanone prepared in EXAMPLE 4. To the homogeneous solution, 450.2 mg (1 equivalent) of oxalic acid was added, and the mixture was stirred for 1 hour at 15° C. to precipitate crystals. The crystals were filtered off under a reduced pressure. White crystals of (2R)-1-[4-(benzyloxy)phenyl]-2-[((1R)-phenylethyl)amino]-1-propanone oxalate were obtained as a result (1,632.8 mg, isolation yield: 69%). The diastereomer ratio thereof was determined as in EXAMPLE 3. The ratio, (2S)-isomer/(2R)-isomer, was 43.3/56.7 (13.4% d.e.).

EXAMPLE (SYNTHETIC EXAMPLE) OF ISOLATING AN OPTICALLY ACTIVE α-SUBSTITUTED AMINOKETONE SALT (5) BY ADDING A SOLVENT TO A DIASTEREOMER MIXTURE (3) OF OPTICALLY ACTIVE α-SUBSTITUTED AMINOKETONE TO PREPARE A HOMOGENEOUS SOLUTION, PRODUCING A SALT BY ADDING AN ACID, AND PREFERNTIALLY CRYSTALLIZING ONE DIASTEREOMER FROM THE SOLUTION

EXAMPLE 15

Synthesis of (2R)-1-[4-(benzyloxy)phenyl]-2-[((1R)-phenylethyl)amino]-1-propanone hydrochloride A homogeneous solution was prepared by adding 15 mL of ethanol to 2.070 g (5 mmol) of the diastereomer mixture of 1-[4-(benzyloxy)phenyl]-2-[((1R)-phenylethyl)amino]-1-propanone prepared in EXAMPLE 4. To the homogeneous solution, 521.4 mg (1 equivalent) of concentrated hydrochloric acid was added, and the mixture was stirred for 1 hour at 15° C. to precipitate crystals. The crystals were filtered off under a reduced pressure. White crystals of (2R)-1-[4-(benzyloxy)phenyl]-2-[((1R)-phenylethyl)amino]-1-propanone hydrochloride were obtained as a result (924.1 mg, isolation yield: 44%). The diastereomer ratio thereof was determined as in EXAMPLE 3. The ratio, (2S)-isomer/(2R)-isomer, was 1.0/99.0 (98.0% d.e.).

$^1$H-NMR (DMSO, 400 MHz/ppm): δ 1.42 (3H, d), 1.66 (3H, d), 4.36 (1H, brs), 4.65 (1H, brs), 5.22 (2H, s), 7.11 (2H, d), 7.3-7.5 (5H, m), 7.86 (2H, d), 9.59 (1H, brs), 9.91 (1H, brs)

EXAMPLE (SYNTHETIC EXAMPLE) OF ISOLATING AN OPTICALLY ACTIVE α-SUBSTITUTED AMINOKETONE SALT (5) BY ADDING A SOLVENT TO A DIASTEREOMER MIXTURE (3) OF OPTICALLY ACTIVE α-SUBSTITUTED AMINOKETONE TO PREPARE A HOMOGENEOUS SOLUTION, PRODUCING A SALT BY ADDING AN ACID, AND PREFERENTIALLY CRYSTALLIZING ONE DIASTEREOMER FROM THE SOLUTION

EXAMPLE 16

Synthesis of (2R)-1-[4-(benzyloxy)phenyl]-2-[((1R)-phenylethyl)amino]-1-propanone hydrobromide A homogeneous solution was prepared by adding 15 mL of ethanol to 2.070 g (5 mmol) of the diastereomer mixture of 1-[4-(benzyloxy)phenyl]-2-[((1R)-phenylethyl)amino]-1-propanone prepared in EXAMPLE 4. To the homogeneous solution, 860.9 mg (1 equivalent) of 47 wt % hydrobromic acid was added, and the mixture was stirred for 1 hour at 15° C. to precipitate crystals. The crystals were filtered off under a reduced pressure. White crystals of (2R)-1-[4-(benzyloxy)phenyl]-2-[((1R)-phenylethyl)amino]-1-propanone hydrobromide were obtained as a result (1,019.9 mg, isolation yield: 46%). The diastereomer ratio thereof was determined as in EXAMPLE 3. The ratio, (2S)-isomer/(2R)-isomer, was 1.8/98.2 (96.4% d.e.).

$^1$H-NMR (DMSO, 400 MHz/ppm): δ 1.39 (3H, d), 1.63 (3H, d), 4.37 (1H, brs), 4.72 (1H, brs), 5.23 (2H, s), 7.13 (2H, d), 7.3-7.5 (5H, m), 7.91 (2H, d), 9.47 (2H, brs)

EXAMPLE OF SYNTHESIZING OPTICALLY ACTIVE β-SUBSTITUTED ACTIVE ALCOHOL (6) BY STEREOSELECTIVELY REDUCING OPTICALLY ACTIVE α-SUBSTITUTED AMINOKETONE SALT (5)

EXAMPLE 17

Synthesis of (1R,2S)-1-[4-(benzyloxy)phenyl]-2-[((1R)-phenylethyl)amino]-1-propanol A toluene solution (20 mL) of 4.556 g (10 mmol) of (2S)-1-[4-(benzyloxy)phenyl]-2-[((1R)-phenylethyl)amino]-1-propanone methanesulfonate synthesized in EXAMPLE 3 was washed with 20 mL of a saturated sodium hydrogen carbonate solution. To the resulting solution, 5 mL of ethanol and 189 mg (0.5 equivalent) of sodium borohydride were added at 15° C., and the mixture was stirred for 1 hour. The reaction was terminated by adding 3 mL of 3 N hydrochloric acid. Extraction was then conducted by adding 3 mL of a 20 wt % sodium hydroxide aqueous solution. The organic layer was washed with 10 mL of water twice, dried over anhydrous magnesium sulfate, and subjected to distillation under a reduced pressure to remove the solvents. As a result, (1R,2S)-1-[4-(benzyloxy)phenyl]-2-[((1R)-phenylethyl)amino]-1-propanol was obtained as a colorless oily substance (4.281 g, reaction yield: 87%). The diastereomer ratio thereof was determined by high-performance liquid chromatography (column: Daicel Chiralpak AD 4.6×250 mm, eluent: hexane/isopropanol=10/1, flow: 1.0 mL/min, column temperature: 35° C., detector: UV 210 nm, retention time: (1R,2S)-isomer=12.3 min., (1S,2S)-isomer=11.0 min). The ratio, (1R,2S)-isomer/(1S,2S)-isomer, was 82.1/17.9.

$^1$H-NMR (DMSO, 400 MHz/ppm): δ 0.91 (3H, d), 1.42 (3H, d), 2.5-3.4 (1H, brs), 2.79 (1H, dq), 3.95 (1H, q), 4.52 (1H, s), 5.05 (2H, s), 6.91 (2H, d), 7.15 (2H, d), 7.2-7.5 (10H, m)

EXAMPLE OF SYNTHESIZING OPTICALLY ACTIVE β-SUBSTITUTED AMINO ALCOHOL (6) BY STEREOSELECTIVELY REDUCING OPTICALLY ACTIVE α-SUBSTITUTED AMINOKETONE SALT (5)

EXAMPLE 18

Synthesis of (1R,2S)-1-[4-(benzyloxy)phenyl]-2-[((1R)-phenylethyl)amino]-1-propanol To an ethanol solution (10 mL) of 2.317 g (5 mmol) of (2S)-1-[4-(benzyloxy)phenyl]-2-[((1R)-phenylethyl)amino]-1-propanone methanesulfonate synthesized in EXAMPLE 3, 290 mg (1.5 equivalent) of sodium borohydride was added at 15° C., and the solution was stirred for 1 hour. The reaction was terminated by adding 5 mL of 3 N hydrochloric acid. Extraction was then conducted by adding 20 mL of ethyl acetate and 4 mL of a 20 wt % sodium hydroxide aqueous solution. The organic layer was washed with 10 mL of water twice, dried over anhydrous magnesium sulfate, and subjected to distillation under a reduced pressure to remove the solvents. As a result, (1R,2S)-1-[4-(benzyloxy)phenyl]-2-[((1R)-phenylethyl)amino]-1-propanol was obtained as a colorless oily substance (1.9852 g, reaction yield: 85%). The diastereomer ratio thereof was determined as in EXAMPLE 17. The ratio, (1R,2S)-isomer/(1S,2S)-isomer, was 92.4/7.6.

EXAMPLE OF SYNTHESIZING OPTICALLY ACTIVE β-SUBSTITUTED AMINO ALCOHOL (6) BY STEREOSELECTIVELY REDUCING OPTICALLY ACTIVE α-SUBSTITUTED AMINOKETONE SALT (5)

EXAMPLE 19

Synthesis of (1R,2S)-1-[4-(benzyloxy)phenyl]-2-[((1R)-phenylethyl)amino]-1-propanol To an ethanol solution (10 mL) of 2.317 g (5 mmol) of (2S)-1-[4-(benzyloxy)phenyl]-2-[((1R)-phenylethyl)amino]-1-propanone methanesulfonate synthesized in EXAMPLE 3 and water (1 mL), 385 mg (2 equivalents) of sodium borohydride was added at 15° C., and the mixture was stirred for 1 hour. The reaction was terminated by adding 5 mL of 3 N hydrochloric acid. Extraction was then conducted by adding 20 mL of ethyl acetate and 4 mL of a 20 wt % sodium hydroxide aqueous solution. The organic layer was washed with 10 mL of water twice, dried over anhydrous magnesium sulfate, and subjected to distillation under a reduced pressure to remove the solvent. (1R,2S)-1-[4-(Benzyloxy)phenyl]-2-[((1R)-phenylethyl)amino]-1-propanol was obtained as a colorless oily substance (2.571 g, reaction yield: 83%). The diastereomer ratio thereof was determined as in EXAMPLE 17. The ratio, (1R,2S)-isomer/(1S,2S)-isomer, was 95.3/4.7.

EXAMPLE OF SYNTHESIZING OPTICALLY ACTIVE β-SUBSTITUTED AMINO ALCOHOL (6) BY STEREOSELECTIVELY REDUCING OPTICALLY ACTIVE α-SUBSTITUTED AMINOKETONE SALT (5)

EXAMPLE 20

Synthesis of (1S,2R)-1-[4-(benzyloxy)phenyl]-2-[((1R)-phenylethyl)amino]-1-propanol To an ethanol solution (5 mL) of 738 mg (2 mmol) of (2R)-1-[4-(benzyloxy)phenyl]-2-[((1R)-phenylethyl)amino]-1-propanone hydrochloride synthesized in EXAMPLE 15, 151.3 mg (2 equivalents) of sodium borohydride was added at 15° C., followed by 1 hour of stirring. Subsequently, 4 mL of a 3 N hydrochloric acid was added to conduct quenching, and extraction was performed by adding 30 mL of toluene and 3 mL of a 20 wt % sodium hydroxide aqueous solution. The organic layer was washed with 10 mL of saturated brine, dried over anhydrous magnesium sulfate, and subjected to distillation under a reduced pressure to remove the solvents. (1S,2R)-1-[4-(Benzyloxy)phenyl]-2-[((1R)-phenylethyl)amino]-1-propanol was obtained as a colorless oily substance (906.8 mg, reaction yield: 74%). The diastereomer ratio thereof was determined by high-performance liquid chromatography (column: Daicel Chiralpak AD 4.6×250 mm, eluent: hexane/isopropanol=10/1, flow: 1.0 mL/min, column temperature: 35° C., detector: UV 210 nm, retention time: (1S,2R)-isomer=9.9 min., (1R,2R)-isomer=12.4 min). The ratio, (1S,2R)-isomer/(1R,2S)-isomer, was 84.3/15.7.

EXAMPLE OF SYNTHESIZING OPTICALLY ACTIVE β-SUSTITUTED AMINO ALCOHOL (6) BY STEREOSELECTIVELY REDUCING OPTICALLY ACTIVE α-SUBSTITUTED AMINOKETONE SALT (5)

EXAMPLE 21

Synthesis of (1S,2R)-1-[4-(benzyloxy)phenyl]-2-[((1S)-phenylethyl)amino]-1-propanol To an ethanol solution (5 mL) of 227.8 mg (0.5 mmol) of (2R)-1-[4-(benzyloxy)phenyl]-2-[((1S)-phenylethyl)amino]-1-propanone methanesulfonate, 37.7 mg (2 equivalents) of sodium borohydride was added at 15° C., followed by 1 hour of stirring. The reaction was terminated by adding 3 mL of 3 N hydrochloric acid. Extraction was then conducted by adding 30 mL of ethyl acetate and 2 mL of a 20 wt % sodium hydroxide aqueous solution. The organic layer was washed with 10 mL of saturated brine, dried over anhydrous magnesium sulfide, and subjected to distillation under a reduced pressure to remove the solvents. (1S,2R)-1-[4-(Benzyloxy)phenyl]-2-[((1S)-phenylethyl)amino]-1-propanol was obtained as a colorless oily substance (182.1 mg, reaction yield: 93%). The diastereomer ratio of this substance was determined by high-performance liquid chromatography (column: YMC ODS-A A-303 4.6×50 mm, eluent: acetonitrile/1 mM phosphoric acid buffer solution (pH=2.5)=1/1, flow: 0.5 mL/min, column temperature: 40° C., detector: UV 210 nm, retention time: (1S,2R)-isomer=8.1 min., (1R,2R)-isomer=9.0 min). The ratio, (1S,2R)-isomer/(1R,2R)-isomer, was 92/8.

EXAMPLE OF SYNTHESIZING OPTICALLY ACTIVE β-AMINO ALCOHOL (7) BY HYDROGENOLYSIS OF OPTICALLY ACTIVE β-SUBSTITUTED AMINO ALCOHOL (6)

EXAMPLE 22

(1R,2S)-1-(4-hydroxyphenyl)-2-amino-1-propanol

To a solution of 2.571 g (4.3 mmol) of (1R,2S)-1-[4-(benzyloxy)phenyl]-2-[((1R)-phenylethyl)amino]-1-propanol synthesized in EXAMPLE 19 in tetrahydrofuran (2 mL) and ethanol (8 mL), 100 mg of 10% Pd/C was added. The resulting mixture was stirred under a hydrogen atmosphere at 3 atm and 35° C. for 6 days. After the catalyst was filtered off, the solvent was distilled off under a reduced pressure to obtain (1R,2S)-1-(4-hydroxyphenyl)-2-amino-1-propanol as a viscous oily substance (reaction yield: 100%). The optical purity and the diastereomer ratio of this substance were determined by high-performance liquid chromatography (column: Daicel CROWNPAK CR(+), 4×150 mm, eluent: aqueous perchloric acid (pH=1), flow: 0.4 mL/min, column temperature: 25° C., detector: UV 210 nm, retention time: (1R,2R)-isomer=9.4 min., (1R,2S)-isomer=9.8 min, (1S,2S)-isomer=11.0 min, and (1S,2R) diastereomer=12.9 min). The optical purity was 95.6% e.e. The ratio, (1R,2S)-isomer/(1S,2S)-isomer, was 95.3/4.7.

$^1$H-NMR (DMSO, 400 MHz/ppm): δ 0.92 (3H, d), 2.91 (1H, m), 2.6-4.0 (4H, Brs), 4.25 (1H, s), 6.72 (2H, d), 7.10 (2H, d)

EXAMPLE OF SYNTHESIZING OPTICALLY ACTIVE β-AMINO ALCOHOL (7) BY HYDROGENEOUS OF OPTICALLY ACTIVE β-SUBSTITUTED AMINO ALCOHOL (6)

EXAMPLE 23

(1S,2R)-1-(4-hydroxyphenyl)-2-amino-1-propanol

To a solution prepared by dissolving 2.571 g (4.3 mmol) of (1S,2R)-1-[4-(benzyloxy)phenyl]-2-[((1R)-phenylethyl)amino]-1-propanol synthesized in EXAMPLE 20 in 2 mL of tetrahydrofuran and 8 mL of ethanol, 100 mg of 10% Pd/C was added, and the resulting mixture was stirred under a hydrogen atmosphere at 3 atm and 35° C. for 6 days. After the catalyst was filtered off, the solvents were distilled off under a reduced pressure to obtain (1S,2R)-1-(4-hydroxyphenyl)-2-amino-1-propanol as a viscous oily substance (reaction yield: 100%). The optical purity and the diastereomer ratio of this substance were determined as in EXAMPLE 22. The optical purity was 99.2% e.e. The ratio, (1S,2R)-isomer/(1R,2R)-isomer, was 86.2/13.8.

EXAMPLE OF SYNTHESIZING OPTICALLY ACTIVE β-AMINO ALCOHOL (7) BY HYDROGENOLYSIS OF OPTICALLY ACTIVE β-SUBSTITUTED AMINO ALCOHOL (6)

EXAMPLE 24

(1S,2R)-1-(4-hydroxyphenyl)-2-amino-1-propanol

To a tetrahydrofuran solution (10 mL) of 182 mg (0.46 mmol) of (1S,2R)-1-[4-(benzyloxy)phenyl]-2-[((1S)-phenylethyl)amino]-1-propanol synthesized in EXAMPLE 21, 100 mg of 10% Pd/C was added. The resulting mixture was stirred under a hydrogen atmosphere at 3 atm and 35° C. for 3 days. After the catalyst was filtered off, the solvent was distilled off under a reduced pressure to obtain (1S,2R)-1-(4-hydroxyphenyl)-2-amino-1-propanol as a viscous oily substance (reaction yield: 78%). The optical purity and the diastereomer ratio of this substance were determined as in EXAMPLE 22. The optical purity was 100% e.e. The ratio, (1S,2R)-isomer/(1R,2R)-isomer, was 93/7.

SYNTHETIC EXAMPLE OF α-SUBSTITUTED KETONE (1)

Reference Example 2

Synthesis of 1-phenyl-2-bromo-1-propanone

To a methylene chloride solution (5 mL) of 4.934 g (36.82 mmol) of propiophenone, a methylene chloride solution (5 mL) of 6.4873 g (1.1 equivalents) of bromine was gradually added at 15° C., followed by 1 hour of stirring. To the resulting solution, 30 mL of a saturated sodium hydrogen carbonate solution and 40 mL of ethyl acetate were added to conduct extraction. The organic layer was washed with 20 mL of a 20 wt % sodium thiosulfate aqueous solution and then with 20 mL of saturated brine, dried over anhydrous magnesium sulfate, and subjected to distillation under a reduced pressure to remove the solvent. 1-Phenyl-2-bromo-1-propanone was obtained as an yellow, oily substance (8.7633 g, crude yield: 92%).

SYNTHETIC EXAMPLE OF OPTICALLY ACTIVE α-SUBSTITUTED AMINOKETONE SALT (5) FROM α-SUBSTITUTED KETONE (1)

EXAMPLE 25

Synthesis of (2S)-1-phenyl-2-[((1R)-phenylethyl)amino]-1-propanone methanesulfonate To an acetonitrile solution (30 mL) of 8.76 g (33.87 mmol) of 1-phenyl-2-bromo-1-propanone synthesized in REFERENCE EXAMPLE 2 and 7.448 g (73.6 mmol) of triethylamine, 5.351 g (44.2 mmol) of (R)-phenethylamine was added, and the resulting solution was stirred for 16 hours at 40° C. After 20 mL of water was added, the solvents were distilled off under a reduced pressure, and 40 mL of ethyl acetate was added to conduct extraction. The organic layer was washed with 20 mL of a saturated sodium hydrogen carbonate solution twice, dried over anhydrous magnesium sulfate, and subjected to distillation under a reduced pressure to obtain a diastereomer mixture of 1-phenyl-2-[((1R)-phenylethyl)amino]-1-propanone as a red, oily substance (10.63 g, reaction yield: 79%). A homogeneous solution was prepared using 20 mL of ethyl acetate. To the homogeneous solution, 3.364 g (35 mmol) of methanesulfonic acid was added, followed by 1 hour of stirring at 15° C. to precipitate crystals. The crystals were filtered off under a reduced pressure. White crystals of (2S)-1-phenyl-2-[((1R)-phenylethyl)amino]-1-propanone methanesulfonate were obtained as a result (5,232.9 mg, isolation yield: 40%). The diastereomer ratio of this substance was determined by high-performance liquid chromatography (column: Daicel Chiralpak AD 4.6× 250 mm, eluent: hexane/isopropanol=10/1, flow: 0.5 mL/min, column temperature: 35° C., detector: UV 210 nm, retention time: (2S)-isomer=8.7 min., (2R)-isomer=7.4 min). The ratio (2S)-isomer/(2R)-isomer was 97.2/2.8 (94.4% d.e.).

¹H-NMR (CDCl₃, 400 MHz/ppm): δ 1.71 (3H, d), 1.92 (3H, d), 2.83 (3H, s), 4.58 (1H, m), 4.87 (1H, m), 7.27 (3H, m), 7.44 (2H, m), 7.54 (2H, m), 7.58 (1H, m), 7.71 (2H, m), 8.61 (1H, brs), 9.90 (1H, brs)

EXAMPLE OF SYNTHESIZING β-SUBSTITUTED AMINO ALCOHOL (6) BY STEREOSELECTIVELY REDUCING OPTICALLY ACTIVE α-SUBSTITUTED AMINOKETONE SALT (5)

EXAMPLE 26

Synthesis of (1R,2S)-1-phenyl-2-[((1R)-phenylethyl)amino]-1-propanol

To an ethanol solution (10 mL) of 1,745 mg (5 mmol) (2S)-1-phenyl-2-[((1R)-phenylethyl)amino]-1-propanone methanesulfonate synthesized in EXAMPLE 25, 378 mg (2 equivalents) of sodium borohydride was added at 15° C., followed by 1 hour of stirring. The reaction was terminated by adding 5 mL of 3 N hydrochloric acid. To the resulting solution, 40 mL of ethyl acetate and 4 mL of a 20 wt % sodium hydroxide aqueous solution were added to perform extraction. The organic layer was washed with 20 mL of water, dried over anhydrous magnesium sulfate, and subjected to distillation under a reduced pressure to remove the solvent. (1R,2S)-1-Phenyl-2-[((1R)-phenylethyl)amino]-1-propanol was obtained as a colorless, oily substance (1.3192 g, crude yield 100%). The diastereomer ratio thereof was determined by high-performance liquid chromatography (column: Daicel Chiralpak AD 4.6×250 mm, eluent: hexane/isopropanol=10/1, flow: 1.0 mL/min, column temperature: 35° C., detector: UV 210 nm, retention time: (1R,2S)-isomer=12.6 min., (1S,2S)-isomer=11.8 min). The ratio, (1R,2S)-isomer/(1S,2S)-isomer was 93.4/6.6.

¹H-NMR (CDCl₃, 400 MHz/ppm): δ 0.87 (3H, d), 1.37 (3H, d), 1.6-2.4 (2H, brs), 2.82 (1H, m), 3.92 (1H, q), 4.46 (1H, d), 7.22-7.34 (10H, m)

EXAMPLE OF SYNTHESIZING OPTICALLY ACTIVE β-AMINO ALCOHOL (7) BY HYDROGENOLYSIS OF OPTICALLY ACTIVE β-SUBSTITUTED AMINO ALCOHOL (6)

EXAMPLE 27

(1R,2S)-1-phenyl-2-amino-1-propanol hydrochloride

To a tetrahydrofuran solution (20 mL) of 1.319 g (5 mmol) of (1R,2S)-1-phenyl-2-[((1R)-phenylethyl)amino]-1-propanol synthesized in EXAMPLE 26, 500 mg of 10% Pd/C was added, and the resulting solution was stirred under a hydrogen atmosphere at 3 atm at 35° C. for 6 days. After the catalyst was filtered off, the solvent was distilled off under a reduced pressure to obtain (1R,2S)-1-phenyl-2-amino-1-propanol as a colorless oily substance (reaction yield: 75%).

To the substance, 40 mL of ethanol and 2 mL of 3 N hydrochloric acid were added, and the solvents were distilled off under a reduced pressure to obtain an oily substance. To this substance, 1.5 mL of ethanol and 10 mL of diisopropyl ether were added to precipitate crystals. White crystals of (1R,2S)-1-phenyl-2-amino-1-propanol hydrochloride were obtained as a result (490.3 mg, isolation yield: 40%). The optical purity and the diastereomer ratio thereof were determined by high-performance liquid chromatography (column: Daicel CROWNPAK CR(+), 4×150 mm, eluent: aqueous perchloric acid (pH=1), flow: 0.5 mL/min, column temperature: 25° C., detector: UV 210 nm, retention time: (1R,2S)-isomer=10.6 min, and (1S,2S)-isomer=11.7 min, (1S,2R)-isomer=14.1 min). The optical purity was 97.0% e.e. The ratio, (1R,2S)-isomer/(1S,2S)-isomer was 92.9/7.1.

¹H-NMR (DMSO, 400 MHz/ppm): δ 0.98 (3H, d), 5.02 (1H, s), 5.98 (1H, s), 7.26-7.36 (5H, m), 8.17 (3H, brs)

SYNTHETIC EXAMPLE OF α-SUBSTITUTED KETONE (1)

Reference Example 3

Synthesis of 1-phenyl-2-bromo-1-butanone

To a tetrahydrofuran solution (20 mL) of 9.917 g (67.0 mmol) of butyrophenone, a hexane solution (10 mL) of 11.78 g (1.1 equivalents) of bromine was gradually added at 5° C. The temperature was elevated to 15° C., and the solution was stirred for 1 hour. To the solution, 20 mL of water and 40 mL of ethyl acetate were added to conduct extraction. The organic layer was washed with 30 mL of a saturated sodium hydrogen carbonate solution three times, dried over anhydrous magnesium sulfate, and subjected to distillation under a reduced pressure to remove the solvents. 1-Phenyl-2-bromo-1-butanone was obtained as a light peach-colored oily substance (23.94 g, crude yield: 92%).

SYTHENTIC EXAMPLE OF OPTICALLY ACTIVE α-SUBSTITUTED AMINO KETONE SALT (5) FROM α-SUBSTITUTED KETONE (1)

EXAMPLE 28

Synthesis of (2S)-1-phenyl-2-[((1R)-phenylethyl)amino]-1-butanone methanesulfonate To an acetonitrile solution (30 mL) of 12.07 g (31.1 mmol) 1-phenyl-2-bromo-1-butanone synthesized in REFERENCE EXAMPLE 3 and 6.294 g (2 equivalents) of triethylamine, 4.522 g (1.2 equivalents) of (R)-phenethylamine was added. The resulting solution was stirred at 40° C. for 16 hours. After 30 mL of water was added to the solution, the solvent was distilled off under a reduced pressure, and 50 mL of ethyl acetate was added to conduct extraction. The organic layer was washed with 30 mL of a saturated sodium hydrogen carbonate solution and then with 20 mL of saturated brine, dried over anhydrous magnesium sulfate, and subjected to distillation under a reduced pressure to remove the solvents. A diastereomer mixture of 1-phenyl-2-[((1R)-phenylethyl)amino]-1-butanone was obtained as an yellow, oily substance (11.27 g, reaction yield: 85%). A homogeneous solution was prepared using 30 mL of ethyl acetate. To the homogeneous solution, 2.986 g (1 equivalent) of methanesulfonic acid was added, and the resulting mixture was stirred at 15° C. for 1 hour to precipitate crystals. The crystals are filtered off under a reduced pressure. White crystals of (2S)-1-phenyl-2-[((1R)-phenylethyl)amino]-1-butanone methanesulfonate were obtained as a result (4,243.2 mg, isolation yield: 36%). The diastereomer ratio thereof was determined by high-performance liquid chromatography (column: Daicel Chiralpak AD 4.6×250 mm, eluent: hexane/isopropanol=10/1, flow: 0.5 mL/min, column temperature: 35° C., detector: UV 210 nm, retention time: (2S)-isomer=8.0 min., (2R)-isomer=7.1 min). The ratio, (2S)-isomer/(2R)-isomer, was 91.5/8.5 (83.0% d.e.).

¹H-NMR (CDCl₃, 400 MHz/ppm): δ 0.86 (3H, t), 1.94 (3H, d), 2.17 (1H, m), 2.33 (1H, m), 2.88 (3H, s), 4.59 (1H, brs), 4.86 (1H, brs), 7.16-7.26 (3H, m), 7.40-7.53 (3H, m), 7.59 (2H, d), 7.67 (2H, d), 7.87 (1H, brs), 10.30 (1H, brs)

EXAMPLE OF SYNTHESIZING OPTICALLY ACTIVE β-SUBSTITUTED AMINO ALCOHOL (6) BY STEREOSELECTIVELY REDUCING OPTICALLY ACTIVE α-SUBSTITUTED AMINOKETONE SALT (5)

EXAMPLE 29

Synthesis of (1R,2S)-1-phenyl-2-[((1R)-phenylethyl)amino]-1-butanol

To a solution of 1,815 mg (5 mmol) of (2S)-1-phenyl-2-[((1R)-phenylethyl)amino]-1-butanone methanesulfonate synthesized in EXAMPLE 28 in tetrahydrofuran (5 mL) and ethanol (10 mL), 290 mg (1.5 equivalents) of sodium borohydride was added at 15° C., followed by 1 hour of stirring. The reaction was terminated by adding 5 mL of 3 N hydrochloric acid. To the resulting solution, 40 mL of ethyl acetate and 4 mL of a 20 wt % sodium hydroxide aqueous solution were added to conduct extraction. The organic layer was washed with 10 mL of water and then with 20 mL of saturated brine, dried over anhydrous magnesium sulfate, and subjected to distillation under a reduced pressure to remove the solvent. (1R,2S)-1-Phenyl-2-[((1R)-phenylethyl)amino]-1-butanol was obtained as a colorless, oily substance (1.316 g, crude yield: 96%). The diastereomer ratio of this substance was determined by high-performance liquid chromatography (column: Daicel Chiralpak AD 4.6×250 mm, eluent: hexane/isopropanol=10/1, flow: 1.0 mL/min, column temperature: 35° C., detector: UV 210 nm, retention time: (1R,2S)-isomer=6.2 min., (1S,2S)-isomer=5.6 min). The ratio, (1R,2S)-isomer/(1S,2S)-isomer, was 93.3/6.7.

$^1$H-NMR (CDCl$_3$, 400 MHz/ppm): δ 0.87 (3H, t), 1.17 (1H, m), 1.35 (1H, m), 1.39 (3H, d), 2.64 (1H, m), 3.90 (1H, q), 4.46 (1H, d), 7.1-7.4 (10H, m)

EXAMPLE OF SYNTHESIZING OPTICALLY ACTIVE β-AMINO ALCOHOL SALT (7) BY HYDROGENOLYSIS OF OPTICALLY ACTIVE β-SUBSTITUTED AMINO ALCOHOL (6)

EXAMPLE 30

Synthesis of (1R,2S)-1-phenyl-2-amino-1-butanol hydrochloride

To a solution of 1.316 g (4.8 mmol) of (1R,2S)-1-phenyl-2-[((1R)-phenylethyl)amino]-1-butanol synthesized in EXAMPLE 29 in 5 mL of tetrahydrofuran and 10 mL of ethanol, 400 mg of 10% Pd/C was added, and the resulting mixture was stirred under a hydrogen atmosphere at 3 atm and 35° C. for 5 days. After the catalyst was filtered off, the solvents were distilled off under a reduced pressure to obtain (1R,2S)-1-phenyl-2-amino-1-butanol as a colorless, oily substance (reaction yield: 100%). To this substance, 40 mL of ethanol and 1 mL of concentrated hydrochloric acid were added. The solvents were distilled off under a reduced pressure to obtain an oily substance. This substance was then mixed with 1 mL of ethanol and 30 mL of diisopropyl ether to precipitate crystals. White crystals of (1R,2S)-1-phenyl-2-amino-1-butanol hydrochloride were obtained as a result (848.5 mg, isolation yield: 88%). The optical purity and the diastereomer ratio thereof were determined by high-performance liquid chromatography (column: Daicel CROWNPAK CR(+), 4×150 mm, eluent: aqueous perchloric acid (pH=1), flow: 1.0 mL/min, column temperature: 25° C., detector: UV 210 nm, retention time: (1R,2S)-isomer=14.8 min, and (1S,2S)-isomer=19.1 min, (1S,2R)-isomer=30.3 min). The optical purity was 100.0% e.e. The ratio, (1R,2S)-isomer/(1S,2S)-isomer was 80.9/19.1.

$^1$H-NMR (DMSO, 400 MHz/ppm): δ 0.82 (3H, t), 1.45 (2H, m), 3.19 (1H, m), 5.04 (1H, brs), 6.00 (1H, brs), 7.2-7.4 (5H, m), 8.10 (3H, brs)

SYNTHETIC EXAMPLE OF OPTICALLY ACTIVE α-SUBSTITUTED AMINOKETONE SALT (5) FROM α-SUBSTITUTED KETONE (1)

EXAMPLE 31

Synthesis of (2S)-1-[4-(benzyloxy)phenyl]-2-{[(1R)-(4-methoxyphenyl)ethyl]amino}-1-propanone methanesulfonate To an acetonitrile solution (20 mL) of 4.788 g (15 mmol) of 1-[4-(benzyloxy)phenyl]-2-bromo-1-propanone synthesized in REFERENCE EXAMPLE 1 and 3.036 g (2 equivalents) of triethylamine, 2.718 g (1.2 equivalents) of (R)-p-methoxyphenethylamine was added, and the resulting solution was stirred for 7 hours at 40° C. After 10 mL of water was added to the solution, the solvent was distilled off under a reduced pressure, and 30 mL of ethyl acetate was added to conduct extraction. The organic layer was washed with 20 mL of a saturated sodium hydrogen carbonate solution, dried over anhydrous magnesium sulfate, and subjected to distillation under a reduced pressure to remove the solvent. A diastereomer mixture of 1-[4-(benzyloxy)phenyl]-2-{[(1R)-(4-methoxyphenyl)ethyl]amino}-1-propanone was obtained as an yellow, oily substance (6.311 g, reaction yield: 99%). A homogeneous solution was prepared using 50 mL of ethyl acetate. To the homogeneous solution, 1.296 g (0.9 equivalent) of methanesulfonic acid was added, and the resulting mixture was stirred at 15° C. for 1 hour to precipitate crystals. The crystals were filtered off under a reduced pressure. White crystals of (2S)-1-[4-(benzyloxy)phenyl]-2-{[(1R)-(4-methoxyphenyl)ethyl]amino}-1-propanone methanesulfonate (3,332 mg, isolation yield: 44%) were obtained. The diastereomer ratio of this substance was determined by high-performance liquid chromatography (column: Daicel Chiralpak AD 4.6×250 mm, eluent: hexane/isopropanol=10/1, flow: 0.5 mL/min, column temperature: 35° C., detector: UV 210 nm, retention time: (2S)-isomer=19.9 min., (2R)-isomer=15.6 min). The ratio, (2S)-isomer/(2R)-isomer, was 98.4/1.6 (96.8% d.e.).

$^1$H-NMR (CDCl$_3$, 400 MHz/ppm): δ 1.69 (3H, d), 1.86 (3H, d), 2.84 (3H, d), 3.66 (3H, d), 4.52 (1H, brs), 4.83 (1H, brs), 5.13 (2H, s), 6.73 (2H, d), 6.96 (2H, d), 7.40 (7H, m), 7.70 (2H, d), 7.97 (1H, brs), 10.03 (1H, brs)

EXAMPLE OF SYNTHESIZING OPTICALLY ACTIVE β-SUBSTITUTED AMINO ALCOHOL (6) BY STEREOSELECTIVELY REDUCING OPTICALLY ACTIVE α-SUBSTITUTED AMINOKETONE SALT (5)

EXAMPLE 32

Synthesis of (1R,2S)-1-[4-(benzyloxy)phenyl]-2-{[(1R)-(4-methoxyphenyl)ethyl]amino}-1-propanol To an ethanol solution (10 mL) of 2,847 mg (5.9 mmol) of (2S)-1-[4-(benzyloxy)phenyl]-2-{[(1R)-(4-methoxyphenyl)

ethyl]amino}-1-propanone methanesulfonate synthesized in EXAMPLE 31, 335 mg (1.5 equivalents) of sodium borohydride was added at 15° C., followed by 1 hour of stirring. The reaction was terminated by adding 5 mL of 3 N hydrochloric acid. Extraction was conducted by adding 30 mL of ethyl acetate and 4 mL of a 20 wt % sodium hydroxide aqueous solution. The organic layer was washed with 10 mL of water and then 10 mL of saturated brine, dried over anhydrous magnesium sulfate, and subjected to distillation under a reduced pressure to remove the solvents. (1R,2S)-1-[4-(Benzyloxy)phenyl]-2-{[(1R)-(4-methoxyphenyl)ethyl]amino}-1-propanol was obtained as a colorless, oily substance (2.523 g, crude yield: 99%).

$^1$H-NMR (CDCl$_3$, 400 MHz/ppm): δ 0.88 (3H, d), 1.33 (3H, d), 2.76 (1H, dq), 3.84 (3H, s), 3.86 (1H, q), 4.38 (1H, d), 5.05 (2H, s), 6.86 (2H, d), 6.92 (2H, d), 7.15 (2H, d), 7.19 (2H, d), 7.3-7.5 (5H, m)

EXAMPLE OF SYNTHESIZING OPTICALLY ACTIVE β-SUBSTITUTED AMINO ALCOHOL (6) BY DEPROTECTING OPTICALLY ACTIVE β-SUBSTITUTED AMINO ALCOHOL (6)

EXAMPLE 33

Synthesis of (1R,2S)-1-[4-(hydroxy)phenyl]-2-{[(1R)-(4-methoxyphenyl)ethyl]amino}-1-propanol To a tetrahydrofuran solution (10 mL) of 2.523 g (5.9 mmol) of (1R,2S)-1-[4-(benzyloxy)phenyl]-2-{[(1R)-(4-methoxyphenyl)ethyl]amino}-1-propanol synthesized in EXAMPLE 32, 200 mg of 10% Pd/C was added. The resulting mixture was stirred under a hydrogen atmosphere at 1 atm and 15° C. for 4 days. After the catalyst was filtered off, the solvent was distilled off under a reduced pressure to obtain (1R,2S)-1-[4-(hydroxy)phenyl]-2-{[(1R)-(4-methoxyphenyl)ethyl]amino}-1-propanol as a light yellow solid (1.4981 g, crude yield: 84%).

$^1$H-NMR (CDCl$_3$, 400 MHz/ppm): δ 0.88 (3H, d), 1.33 (3H, d), 2.0-3.0 (3H, brs), 2.75 (1H, dq), 3.80 (3H, s), 3.85 (2H, q), 4.38 (1H, d), 6.76 (2H, d), 6.86 (2H, d), 7.08 (2H, d), 7.19 (2H, d)

SYNTHETIC EXAMPLE OF OPTICALLY ACTIVE β-AMINO ALCOHOL (7) FROM OPTICALLY ACTIVE α-SUBSTITUTED AMINOKETONE SALT (5)

EXAMPLE 34

(1R,2S)-1-(4-hydroxyphenyl)-2-amino-1-propanol

An ethyl acetate solution (30 mL) of 1.367 g (3 mmol) of (2S)-1-[4-(benzyloxy)phenyl]-2-[((1R)-phenylethyl)amino]-1-propanone methanesulfonate synthesized in EXAMPLE 3 was washed by adding 20 mL of a saturated sodium hydrogen carbonate solution. After the water layer was removed, the residue was dried over anhydrous magnesium sulfate and the solvent was distilled off under a reduced pressure to obtain a colorless, oily substance. To this substance, 500 mg of 10% Pd/C, 6 mL of tetrahydrofuran, and 10 mL of ethanol were added, and the resulting mixture was stirred under a hydrogen atmosphere at 3 atm and 30° C. for 4 days. After the catalyst was filtered out, the solvents were distilled off under a reduced pressure to obtain (1R,2S)-1-(4-hydroxyphenyl)-2-amino-1-propanol as a viscous oily substance (reaction yield: 80%). The optical purity and the diastereomer ratio of this substance were determined as in EXAMPLE 22. The optical purity was 97.6% e.e. The ratio, (1R,2S)-isomer/(1S,2S)-isomer, was 91.9/8.1.

SUNTHETIC EXAMPLE OF OPTICALLY ACTIVE β-AMINO ALCOHOL (7) FROM OPTICALLY ACTIVE α-SUBSTITUTED AMINOKETONE SALT (5)

EXAMPLE 35

(1S,2R)-1-(4-hydroxyphenyl)-2-amino-1-propanol

An ethyl acetate solution (20 mL) of 1.367 g (3 mmol) of (2R)-1-[4-(benzyloxy)phenyl]-2-[((1R)-phenylethyl)amino]-1-propanone hydrobromide synthesized in EXAMPLE 16 was washed by adding 10 mL of a saturated sodium hydrogen carbonate solution. After the water layer was removed, the residue was dried over anhydrous magnesium sulfate and the solvent was distilled off under a reduced pressure to obtain a colorless, oily substance. To this substance, 200 mg of 10% Pd/C, 3 mL of tetrahydrofuran, and 10 mL of ethanol were added, and the resulting mixture was stirred under a hydrogen atmosphere at 4 atm and 30° C. for 3 days. After the catalyst was filtered out, the solvents were distilled off under a reduced pressure to obtain (1S,2R)-1-(4-hydroxyphenyl)-2-amino-1-propanol as a viscous oily substance. The optical purity and the diastereomer ratio of this substance were determined as in EXAMPLE 22. The optical purity was 96.4% e.e. The ratio, (1S,2R)-isomer/(1R,2R)-isomer, was 86.3/13.7.

SYNTHETIC EXAMPLE OF α-SUBSTITUTED KETONE (1)

Reference Example 4

Synthesis of 1-[4-(methanesulfonyloxy)phenyl]-2-bromo-1-propanone

A tetrahydrofuran solution (50 mL) of 15.0 g (100 mmol) of p-hydroxypropiophenone and 12.143 g (1.2 equivalents) of triethylamine was cooled to 5° C. To this solution, 12.60 g (1.1 equivalents) of methanesulfonyl chloride was added dropwise over 30 minutes, followed by 1 hour of stirring. To the resulting solution, 40 mL of water and 70 mL of ethyl acetate were added to conduct extraction. The organic layer was washed with 50 mL of saturated brine, dried over anhydrous magnesium sulfate, and subjected to distillation under a reduced pressure to remove the solvents. A white solid was obtained as a result. This white solid was crystallized from 40 mL of ethyl acetate and 120 mL of hexane to thereby obtain white crystals of p-(methanesulfonyloxy)propiophenone (21.17 g, isolation yield: 93%). To a tetrahydrofuran solution (20 mL) of 4.560 g (20 mmol) of p-(methanesulfonyloxy)propiophenone, a hexane solution (5 mL) of 3.516 g (1.1 equivalent) of bromine was added at 15° C., followed by 1 hour of stirring. To the resulting solution, 30 mL of saturated sodium hydrogen carbonate and 30 mL of ethyl acetate were added to conduct extraction. The organic layer was washed with 20 mL of a saturated sodium hydrogen carbonate solution, dried over anhydrous magnesium sulfate, and subjected to distillation under a reduced pressure to remove the solvent. 1-[4-(Methanesulfonyloxy)phenyl]-2-bromo-1-propanone was obtained as an yellow, oily substance (10.12 g, crude yield: 97%).

$^1$H-NMR (CDCl$_3$, 400 MHz/ppm): δ 1.91 (3H, d), 3.21 (3H, s), 5.23 (1H, q), 7.40 (2H, d), 8.10 (2H, d)

SYNTHETIC EXAMPLE OD OPTICALLY ACTIVE α-SUBSTITUTED AMINOKETONE SALT (5) FROM α-SUBSTITUTED KETONE (1)

EXAMPLE 36

Synthesis of (2S)-1-[4-(methanesulfonyloxy)phenyl]-2-[((1R)-phenylethyl)amino]-1-propanone methanesulfonate To an acetonitrile solution (20 mL) of 3.07 g (10 mmol) of 1-[4-(methanesulfonyloxy)phenyl]-2-bromo-1-propanone synthesized in REFERENCE EXAMPLE 4 and 2.024 g (2 equivalents) of triethylamine, 1.452 g (1.2 equivalents) of (R)-phenethylamine was added, and the resulting mixture was stirred at 15° C. for 16 hours. After 10 mL of water was added, the solvent was distilled off under a reduced pressure, and 30 mL of ethyl acetate was added to conduct extraction. The organic layer was washed with 20 mL of a saturated sodium hydrogen carbonate solution, dried over anhydrous magnesium sulfate, and subjected to distillation under a reduced pressure to remove the solvent. A diastereomer mixture of 1-[4-(methanesulfonyloxy)phenyl]-2-[((1R)-phenylethyl)amino]-1-propanone was obtained as a light yellow, oily substance (reaction yield: 100%). A homogeneous solution was prepared using 30 mL of ethyl acetate and 5 mL of tetrahydrofuran. To the homogeneous solution, 864 mg (0.9 equivalent) of methanesulfonic acid was added, followed by 1 hour of stirring at 15° C. The crystals thus deposited were filtered off under a reduced pressure to obtain white crystals of (2S)-1-[4-(methanesulfonyloxy)phenyl]-2-[((1R)-phenylethyl)amino]-1-propanone methanesulfonate (2,299.7 mg, isolation yield: 51%). The diastereomer ratio of this substance was determined by NMR spectrometry. The ratio, (2S)-isomer/(2R)-isomer was 100/0 (100% d.e.).

$^1$H-NMR (DMSO, 400 MHz/ppm): δ 1.50 (3H, d), 1.65 (3H, d), 2.37 (3H, s), 3.47 (3H, s), 4.41 (1H, brs), 5.15 (1H, brs), 7.37-7.42 (3H, m), 7.53 (d, 4H), 8.10 (d, 2H), 9.26 (1H, brs), 9.53 (1H, brs)

EXAMPLE OF SYNTHESIZING OPTICALLY ACTIVE β-SUBSTITUTED AMINO ALCOHOL (6) BY STEREOSELECTIVELY REDUCING OPTICALLY ACTIVE α-SUBSTITUTED AMINOKETONE SALT (5)

EXAMPLE 37

Synthesis of (1R,2S)-1-[4-(methanesulfonyloxy)phenyl]-2-[((1R)-phenylethyl)amino]-1-propanol To an ethanol solution (15 mL) of 2.290 g (5.2 mmol) of (2S)-1-[4-(methanesulfonyloxy)phenyl]-2-[((1R)-phenylethyl)amino]-1-propanone methanesulfonate synthesized in EXAMPLE 36, 590 mg (3 equivalents) of sodium borohydride was added at 15° C., followed by 1 hour of stirring. The reaction was terminated by adding 5 mL of 3 N hydrochloric acid. Extraction was then conducted by adding 40 mL of ethyl acetate and 30 mL of a saturated sodium hydrogen carbonate solution. The organic layer was washed with 20 mL of a saturated sodium hydrogen carbonate solution, dried over anhydrous magnesium sulfate, and subjected to distillation under a reduced pressure to remove the solvents. (1R,2S)-1-[4-(Methanesulfonyloxy)phenyl]-2-[((1R)-phenylethyl)amino]-1-propanol was obtained as a colorless oily substance (1.8299 g, reaction yield: 84%). The diastereomer ratio of this substance was determined by NMR spectrometry. The ratio, (1R,2S)-isomer/(1S,2S)-isomer was 92/8.

$^1$H-NMR (CDCl$_3$, 400 MHz/ppm): δ 0.87 (3H, d), 1.38 (3H, d), 2.82 (1H, m), 3.10 (1H, d), 3.12 (3H, s), 3.3-3.7 (1H, brs), 3.92 (1H, q), 4.41 (1H, d), 7.2-7.4 (9H, m)

EXAMPLE OF SYNTHESIZING OPTICALLY ACTIVE α-SUBSTITUTED AMINOKETONE SALT (5) FROM α-SUBSTITUTED KETONE (1)

EXAMPLE 38

Synthesis of (2S)-1-[4-(methanesulfonyloxy)phenyl]-2-[((1S)-phenylethyl)amino]-1-propanone hydrochloride To an acetonitrile solution (20 mL) of 3.66 g (11.93 mmol) of 1-[4-(methanesulfonyloxy)phenyl]-2-bromo-1-propanone synthesized in REFERENCE EXAMPLE 4 and 2.414 g (2 equivalents) of triethylamine, 1.735 g (1.2 equivalents) of (S)-phenethylamine was added, and the resulting mixture was stirred at 15° C. for 16 hours. After adding 10 mL of water, the solvent was distilled off under a reduced pressure, and 30 mL of ethyl acetate was added to conduct extraction. The organic layer was washed with 20 mL of a saturated sodium hydrogen carbonate solution, dried over anhydrous magnesium sulfate, and subjected to distillation under a reduced pressure to remove the solvent. A diastereomer mixture of 1-[4-(methanesulfonyloxy)phenyl]-2-[((1S)-phenylethyl)amino]-1-propanone was obtained as a light yellow, oily substance (reaction yield: 78%). A homogeneous solution was prepared using 20 mL of ethanol. To the homogeneous solution, 1.12 g (0.9 equivalent) of concentrated hydrochloric acid was added. The solvent was distilled off under a reduced pressure, and the resulting oily substance was mixed with 15 mL of ethanol, followed by 1 hour of stirring at 15° C. The crystals thus deposited were filtered off under a reduced pressure. White crystals of (2S)-1-[4-(methanesulfonyloxy)phenyl]-2-[((1S)-phenylethyl)amino]-1-propanone hydrochloride were obtained as a result (1.7038 g, isolation yield: 37%). The diastereomer ratio of this substance was determined by NMR spectrometry. The ratio (2S)-isomer/(2R)-isomer was 100/0 (100% d.e.).

$^1$H-NMR (DMSO, 400 MHz/ppm): δ 1.44 (3H, d), 1.67 (3H, d), 3.47 (3H, s), 4.41 (1H, brs), 4.78 (1H, brs), 7.37 (3H, m), 7.49 (2H, d), 7.50 (d, 2H), 8.02 (d, 2H), 9.73 (1H, brs), 10.06 (1H, brs)

EXAMPLE OF SYNTHESIZING OPTICALLY ACTIVE β-AMINO ALCOHOL (7) FROM OPTICALLY ACTIVE α-SUBSTITUTED AMINOKETONE SALT (5)

EXAMPLE 39

(1R,2S)-1-(4-hydroxyphenyl)-2-amino-1-propanol

An ethyl acetate solution (40 mL) of 4.865 g (10.7 mmol) of (2S)-1-[4-(benzyloxy)phenyl]-2-[((1R)-phenylethyl)amino]-1-propanone methanesulfonate synthesized in EXAMPLE 3 was washed by adding 50 mL of a saturated sodium hydrogen carbonate solution. After the water layer was removed, the residue was dried over anhydrous magnesium sulfate and the solvent was distilled off under a reduced pressure to obtain 4.532 g of a colorless, oily substance. To this substance, 500 mg of 20% Pd(OH)$_2$/C (containing 50 wt % of water) and 20 mL of ethanol were added. The mixture was stirred under a hydrogen atmosphere at 1 atm and 15° C. for 5 days. After the catalyst was filtered off, the solvent was distilled off under a reduced pressure to obtain 2.8393 g of (1R,2S)-1-(4-hydroxyphenyl)-2-amino-1-propanol as a viscous oily substance (reaction yield: 87%). The optical purity and the diastereomer ratio of this substance were determined by the method set forth in EXAMPLE 22. The optical purity was 96.6% e.e. The ratio, (1R,2S)-isomer/(1S,2S)-isomer was 90.9/9.1.

SYNTHETIC EXAMPLE OF α-SUBSTITUTED KETONE (1)

Reference Example 5

Synthesis of 1-[4-(benzoyloxy)phenyl]-2-bromo-1-propanone

A tetrahydrofuran solution (40 mL) of 5.00 g (33.3 mmol) of p-hydroxypropiophenone and 3.71 g (1.1 equivalents) of triethylamine was cooled to 5° C. To the resulting solution, 4.92 g (1.05 equivalents) of benzoyl chloride was added dropwise for 30 minutes, followed by 1 hour of stirring. Extraction was conducted by adding 70 mL of water, 5 mL of 3 N hydrochloric acid, and 100 mL of ethyl acetate. The organic layer was washed with 50 mL of a saturated sodium hydrogen carbonate solution and then with 50 mL of water, dried over anhydrous magnesium sulfate, and subjected to distillation under a reduced pressure to remove the solvents. As a result, 8.58 g of a white solid was obtained. The white solid (5.53 g) was crystallized from 30 mL of ethyl acetate and 20 mL of hexane. White crystals of p-(benzoyloxy)propiophenone were obtained as a result (4.77 g, isolation yield: 87%).

To a tetrahydrofuran solution (30 mL) of 3.00 g (11.9 mmol) of the p-(benzoyloxy)propiophenone, a hexane solution (5 mL) of 2.07 g (1.1 equivalents) of bromine was added at 5° C. The temperature of the mixture was elevated to room temperature, followed by 1 hour of stirring. To the resulting mixture, 30 mL of a saturated sodium hydrogen carbonate solution and 40 mL of ethyl acetate were added to conduct extraction. The organic layer was washed with 30 mL of a saturated sodium hydrogen carbonate solution, dried over anhydrous magnesium sulfate, and subjected to distillation under a reduced pressure to remove the solvents. An yellow oily substance (5.54 g) was obtained as a result. This substance was crystallized from 5 mL of ethyl acetate and 30 mL of hexane. White crystals of 1-[4-(benzoyloxy)phenyl]-2-bromo-1-propanone were obtained as a result (3.147 g, isolation yield: 80%).

$^1$H-NMR (CDCl$_3$, 400 MHz/ppm): δ 1.92 (3H, d), 5.28 (1H, q), 7.37 (2H, d), 7.54 (2H, dd), 7.67 (1H, dd), 8.13 (2H, d), 8.20 (2H, d)

SUBSTITUTED EXAMPLE OF OPTICALLY ACTIVE α-SUBSTITUTED AMINOKETONE SALT (5) FROM α-SUBSTITUTED KETONE (1)

EXAMPLE 40

Synthesis of (2S)-1-[4-(benzoyloxy)phenyl]-2-[((1R)-phenylethyl)amino]-1-propanone methanesulfonate To an acetonitrile solution (35 mL) of 7.00 g (10.3 mmol) of 1-[4-(benzoyloxy)phenyl]-2-bromo-1-propanone synthesized in REFERENCE EXAMPLE 5 and 2.08 g (2 equivalents) of triethylamine, 1.37 g (1.1 equivalents) of (R)-phenylethylamine was added, and the resulting mixture was stirred at 40° C. for 20 hours. After 10 mL of water was added, the solvent was distilled off under a reduced pressure, and extraction was conducted by adding 80 mL of ethyl acetate. The organic layer was washed with 30 mL of a saturated sodium hydrogen carbonate solution, dried over anhydrous magnesium sulfate, and subjected to distillation under a reduced pressure to remove the solvent. A diastereomer mixture of 1-[4-(benzoyloxy)phenyl]-2-[((1R)-phenylethyl)amino]-1-propanone was obtained as a light yellow, oily substance (reaction yield: 100%). A homogeneous solution was prepared using 10 mL of ethyl acetate. To the homogeneous solution, 890 mg (0.9 equivalent) of methanesulfonic acid was added, and the mixture was stirred for 1 hour at 15° C. to precipitate crystals. The crystals were filtered off under a reduced pressure. White crystals of (2S)-1-[4-(benzoyloxy)phenyl]-2-[((1R)-phenylethyl)amino]-1-propanone methanesulfonate were obtained as a result (1,143 mg, isolation yield: 24%). The diastereomer ratio thereof was determined by high-performance liquid chromatography (column: Daicel Chiralpak AD 4.6×250 mm, eluent: hexane/isopropanol=10/1, flow: 0.5 mL/min, column temperature: 35° C., detector: UV 210 nm, retention time: (2S)-isomer=18.7 min., (2R)-isomer=14.1 min). The ratio, (2S)-isomer /(2R)-isomer, was 99.8/0.2 (99.6% d.e.).

$^1$H-NMR (CDCl$_3$, 400 MHz/ppm): δ 1.74 (3H, d), 1.94 (3H, d), 2.85 (3H, s), 4.61 (1H, m), 4.93 (1H, m), 7.29 (5H, m), 7.53 (4H, m), 7.67 (1H, dd), 7.83 (2H, d), 8.19 (2H, d), 8.71 (1H, brs), 9.88 (1H, brs)

SYNTHETIC EXAMPLE OF OPTICALLY ACTIVE α-SUBSTITUTED AMINOKETONE SALT (5)

EXAMPLE 41

Synthesis of (2R)-1-[4-(benzoyloxy)phenyl]-2-[((1R)-phenylethyl)amino]-1-propanone hydrochloride The mother liquor for the crystallization obtained in EXAMPLE 40 was condensed under a reduced pressure and mixed with 30 mL of ethyl acetate and 10 mL of a saturated sodium hydrogen carbonate solution to conduct extraction. After the water layer was removed, the residue was dried over anhydrous magnesium sulfate. The solvents were distilled off under a reduced pressure, and a homogeneous solution was prepared by adding 10 mL of ethanol. To the homogeneous solution, 966 mg of concentrated hydrochloric acid was added, and the resulting mixture was stirred for 1 hour at 15° C. to precipitate crystals. The crystals were filtered off under a reduced pressure. White crystals of (2R)-1-[4-(benzoyloxy) phenyl]-2-[((1R)-phenylethyl)amino]-1-propanone hydrochloride were obtained as a result (1,182 mg, isolation yield: 28%). The diastereomer ratio thereof was determined as in EXAMPLE 40. The ratio (2S)-isomer /(2R)-isomer, was 0.3/99.7 (99.4% d.e.).

SYNTHETIC EXAMPLE OF OPTICALLY ACTIVE α-SUBSTITUTED AMINOKETONE (4)

EXAMPLE 42

Synthesis of (2S)-1-(4-hydroxyphenyl)-2-[((1R)-phenylethyl)amino]-1-propanone

To a solution of 1.00 g (2.13 mmol) of (2S)-1-[4-(benzoyloxy)phenyl]-2-[((1R)-phenylethyl)amino]-1-propanone methanesulfonate synthesized in EXAMPLE 40 in 3 mL of water and 7 mL of methanol, 677 mg (2.3 equivalents) of potassium carbonate was added, and the mixture was stirred at 20° C. for 9 hours and 30° C. for 12 hours. Methanol was distilled off under a reduced pressure, and extraction was conducted by adding 30 mL of ethyl acetate and 5 mL of water. The organic layer was washed with 10 ml of water, dried over anhydrous magnesium sulfate, and subjected to distillation under a reduced pressure to remove the solvents. A white solid of (2S)-1-(4-hydroxyphenyl)-2-[((1R)-phenylethyl)amino]-1-propanone was obtained as a result (574 mg, crude yield: 82%).

$^1$H-NMR (CDCl$_3$, 400 MHz/ppm): δ 1.28 (3H, d), 1.37 (3H, d), 3.85 (1H, q), 4.25 (1H, q), 6.84 (2H, d), 7.2-7.5 (5H, d), 7.73 (2H, d)

SYNTHETIC EXAMPLE OF OPTICALLY ACTIVE β-AMINO ALCOHOL (7) FROM OPTICALLY ACTIVE α-SUBSTITUTED AMINOKETONE (4)

EXAMPLE 43

Synthesis of (1R,2S)-1-(4-hydroxyphenyl)-2-amino-1-propanol

A mixture of 200 mg (0.74 mmol) of (2S)-1-(4-hydroxyphenyl)-2-[((1R)-phenylethyl)amino]-1-propanone synthesized in EXAMPLE 42, 50 mg of 20% Pd(OH)$_2$/C (containing 50% of water), and 5 mL of ethanol was stirred under a hydrogen atmosphere at 1 atm and 40° C. for 3 days. After the catalyst was filtered out, the solvent was distilled off under a reduced pressure to thereby obtain 182.4 mg of (1R,2S)-1-(4-hydroxyphenyl)-2-amino-1-propanol as a viscous oily substance (reaction yield: 89%). The optical purity and the diastereomer ratio were determined as in EXAMPLE 22. The optical purity was 100% e.e., and the ratio, (1R,2S)-isomer/(1S,2S)-isomer, was 83.7/16.3.

SYNTHETIC EXAMPLE OF α-SUBSTITUTED KETONE (1)

Reference Example 6

Synthesis of 1-[4-(benzyloxy)phenyl]-2-chloro-1-propanone

To a methylene chloride solution (20 mL) of 4.80 g (20 mmol) of p-(benzyloxy)propiophenone, 2.97 g (1.1 equivalents) of sulfuryl chloride was added at 15° C., followed by 16 hours of stirring. After 20 mL of water was added, methylene chloride was distilled off under a reduced pressure, and extraction was conducted by adding 40 mL of ethyl acetate. The organic layer was washed with 20 mL of a saturated sodium hydrogen carbonate solution, dried over anhydrous magnesium sulfate, and subjected to distillation under a reduced pressure to remove the solvent. A colorless, oily substance (6.299 g) was thereby obtained. The oily substance was crystallized from 0.5 mL of ethyl acetate and 20 mL of hexane to obtain white crystals of 1-[4-(benzyloxy)phenyl]-2-chloro-1-propanone (4.3787 g, isolation yield: 75%).

$^1$H-NMR (CDCl$_3$, 400 MHz/ppm): δ 1.73 (3H, d), 5.15 (2H, s), 5.21 (1H, q), 7.03 (2H, d), 7.3-7.5 (5H, m), 8.00 (2H, d)

SYNTHETIC EXAMPLE OF OPTICALLY ACTIVE α-SUBSTITUTED AMINOKETONE SALT (5) FROM α-SUBSTITUTED KETONE (1)

EXAMPLE 44

Synthesis of (2S)-1-[4-(benzyloxy)phenyl]-2-[((1R)-phenylethyl)amino]-1-propanone methanesulfonate To an acetonitrile solution (20 mL) of 2.745 g (10 mmol) of 1-[4-(benzyloxy)phenyl]-2-chloro-1-propanone synthesized in REFERENCE EXAMPLE 6, 2.024 g (2 equivalents) of triethylamine, and 510 mg (0.5 equivalent) of sodium bromide, 1.454 g (1.2 equivalents) of (R)-phenethylamine was added, and the resulting solution was stirred at 40° C. for 1 week. After 20 mL of water was added, the solvents were distilled off under a reduced pressure, and 40 mL of ethyl acetate was added to conduct extraction. The organic layer was washed with 20 mL of a saturated sodium hydrogen carbonate solution, dried over anhydrous magnesium sulfate, and subjected to distillation under a reduced pressure to remove the solvent. A diastereomer mixture of 1-[4-(benzyloxy)phenyl]-2-[((1R)-phenylethyl)amino]-1-propanone was obtained as a light-yellow oily substance (reaction yield: 68%). Next, a homogeneous solution was prepared using 30 mL of ethyl acetate. To the homogeneous solution, 654 mg (0.7 equivalent) of methanesulfonic acid was added and the resulting mixture was stirred at 15° C. for 1 hour to precipitate crystals. The crystals were filtered off under a reduced pressure. White crystals of (2S)-1-[4-(benzyloxy)phenyl]-2-[((1R)-phenylethyl)amino]-1-propanone methanesulfonate were obtained as a result (1,712,mg, isolation yield: 38%). The diastereomer ratio of this substance was calculated as in EXAMPLE 3. The ratio, (2S)-isomer/(2R)-isomer, was 99.2/0.8 (98.4% d.e.).

EXAMPLE 45

Isolation of (1R,2S)-1-(4-hydroxyphenyl)-2-amino-1-propanol

A 15.7 wt % ethanol solution (6,369 mg) of (1R,2S)-1-(4-hydroxyphenyl)-2-amino-1-propanol synthesized as in EXAMPLE 39 (optical purity: 91.0% e.e. and (1R,2S)/(1S,2S)=88.1/11.9, as determined by the method set forth in EXAMPLE 22) containing 4.80 mmol of the (1R,2S)-isomer was condensed under a reduced pressure. To the resulting viscous oily substance, 1.5 mL of ethanol and 15 mL of methylene chloride were added, followed by 30 minutes of stirring at 5° C. The crystals thus deposited were filtered out. White crystals of (1R,2S)-1-(4-hydroxyphenyl)-2-amino-1-propanol were obtained as a result (the recovery rate of (1R,2S)-isomer: 83%, optical purity: 98.2% e.e., (1R,2S)/(1S,2S)=98.7/1.3).

EXAMPLE 46

Isolation of (1R,2S)-1-(4-hydroxyphenyl)-2-amino-1-propanol

A 15.7 wt % ethanol solution (6,369 mg) of (1R,2S)-1-(4-hydroxyphenyl)-2-amino-1-propanol synthesized as in EXAMPLE 39 (optical purity: 91.0% e.e. and (1R,2S)/(1S,2S)=88.1/11.9, as determined by the method set forth in EXAMPLE 22) containing 4.80 mmol of the (1R,2S)-isomer was condensed under a reduced pressure. To the resulting viscous oily substance, 1 mL of ethanol and 10 mL of ethyl acetate were added, followed by 30 minutes of stirring at 5° C. The crystals thus deposited were filtered out. White crystals of (1R,2S)-1-(4-hydroxyphenyl)-2-amino-1-propanol were obtained as a result (the recovery rate of (1R,2S)-isomer: 52%, optical purity: 98.8% e.e., (1R,2S)/(1S,2S)=99.4/0.6).

EXAMPLE 47

Isolation of (1R,2S)-1-(4-hydroxyphenyl)-2-amino-1-propanol

A 15.7 wt % ethanol solution (6,369 mg) of (1R,2S)-1-(4-hydroxyphenyl)-2-amino-1-propanol synthesized as in EXAMPLE 39 (optical purity: 91.0% e.e. and (1R,2S)/(1S,2S)=88.1/11.9, as determined by the method set forth in EXAMPLE 22) containing 4.80 mmol of the (1R,2S)-isomer was condensed under a reduced pressure. To the resulting viscous oily substance, 1 mL of ethanol and 10 mL of acetonitrile were added, followed by 30 minutes of stirring at 5° C. The crystals thus deposited were filtered out. White crystals of (1R,2S)-1-(4-hydroxyphenyl)-2-amino-1-propanol were obtained as a result (the recovery rate of (1R,2S)-isomer: 54%, optical purity: 98.6% e.e., (1R,2S)/(1S,2S)=99.0/1.0).

EXAMPLE 48

Isolation of (1R,2S)-1-(4-hydroxyphenyl)-2-amino-1-propanol

A 15.7 wt % ethanol solution (6,369 mg) of (1R,2S)-1-(4-hydroxyphenyl)-2-amino-1-propanol synthesized as in EXAMPLE 39 (optical purity: 91.0% e.e. and (1R,2S)/(1S,2S)=88.1/11.9, as determined by the method set forth in EXAMPLE 22) containing 4.80 mmol of the (1R,2S)-isomer was condensed under a reduced pressure. To the resulting viscous oily substance, 1 mL of isopropanol and 10 mL of ethyl acetate were added, followed by 30 minutes of stirring at 5° C. The crystals thus deposited were filtered out. White crystals of (1R,2S)-1-(4-hydroxyphenyl)-2-amino-1-propanol were obtained as a result (the recovery rate of (1R,2S)-isomer: 56%, optical purity: 98.4% e.e., (1R,2S)/(1S,2S)=98.8/1.2).

EXAMPLE 49

Isolation of (1R,2S)-1-(4-hydroxyphenyl)-2-amino-1-propanol hydrochloride

To an ethanol solution of (1R,2S)-1-(4-hydroxyphenyl)-2-amino-1-propanol synthesized as in EXAMPLE 39 (optical purity: 97.6% e.e. and (1R,2S)-isomer/(1S,2S)-isomer=95.1/4.9, as determined by the method set forth in EXAMPLE 22), concentrated hydrochloric acid was added, followed by condensation under a reduced pressure. To the resulting viscous oily substance, methanol was added to prepare a homogeneous solution (1.34 wt % in terms of hydrochloride).

A methanol solution (4,468 mg, (1R,2S)-isomer: 2.77 mmol) of (1R,2S)-1-(4-hydroxyphenyl)-2-amino-1-propanol hydrochloride described above was condensed under a reduced pressure. To the resulting viscous oily substance, 1 mL of ethanol and 10 mL of methylene chloride were added, and the mixture was stirred for 30 minutes at 5° C. to precipitate crystals. The crystals were filtered off under a reduced pressure. White crystals of (1R,2S)-1-(4-hydroxyphenyl)-2-amino-1-propanol hydrochloride were obtained as a result (the recovery rate of the (1R,2S)-isomer: 88%, optical purity: 98.6% e.e., (1R,2S)-isomer/(1S,2S)-isomer=99.1/0.9).

$^1$H-NMR (DMSO, 400 MHz/ppm): δ 0.97 (3H, d), 3.27 (1H, brs), 4.83 (1H, s), 5.84 (1H, d), 6.76 (2H, d), 7.14 (2H, d) 8.02 (3H, brs), 9.48 (1H, s)

EXAMPLE 50

Isolation of (1R,2S)-1-(4-hydroxyphenyl)-2-amino-1-propanol hydrochloride

A methanol solution (4,468 mg, (1R,2S)-isomer: 2.77 mmol) of (1R,2S)-1-(4-hydroxyphenyl)-2-amino-1-propanol hydrochloride described in EXAMPLE 49 was condensed under a reduced pressure to obtain a viscous oily substance. To this substance, 1 mL of ethanol and 10 mL of ethyl acetate were added, and the resulting mixture was stirred at 5° C. for 30 minutes to precipitate crystals. The crystals were filtered off under a reduced pressure. White crystals of (1R,2S)-1-(4-hydroxyphenyl)-2-amino-1-propanol hydrochloride were obtained as a result (the recovery rate of the (1R,2S)-isomer: 79%, optical purity: 98.8% e.e., (1R,2S)-isomer/(1S,2S)-isomer=99.1/0.9).

EXAMPLE 51

Isolation of (1R,2S)-1-(4-hydroxyphenyl)-2-amino-1-propanol hydrochloride

A methanol solution (4,468 mg, (1R,2S)-isomer: 2.77 mmol) of (1R,2S)-1-(4-hydroxyphenyl)-2-amino-1-propanol hydrochloride described in EXAMPLE 49 was condensed under a reduced pressure to obtain a viscous oily substance. To this substance, 1.5 mL of methanol and 10 mL of ethyl acetate were added, and the mixture was stirred for 30 minutes at 5° C. to precipitate crystals. The crystals were filtered off under a reduced pressure to obtain white crystals of (1R,2S)-1-(4-hydroxyphenyl)-2-amino-1-propanol hydrochloride (recovery rate of (1R,2S)-isomer: 47%, optical purity: 99.4% e.e., (1R,2S)-isomer/(1S,2S)-isomer=99.3/0.7).

EXAMPLE 52

Isolation of (1R,2S)-1-(4-hydroxyphenyl)-2-amino-1-propanol hydrochloride

A methanol solution (4,468 mg; (1R,2S)-isomer: 2.77 mmol) of (1R,2S)-1-(4-hydroxyphenyl)-2-amino-1-propanol hydrochloride described in EXAMPLE 49 was condensed under a reduced pressure to obtain a viscous oily substance. To this substance, 2 mL of ethanol and 5 mL of toluene were added, and the mixture was stirred for 30 minutes at 5° C. to precipitate crystals. The crystals were filtered off under a reduced pressure to obtain white crystals of (1R,2S)-1-(4-hydroxyphenyl)-2-amino-1-propanol hydrochloride (recovery rate of (1R,2S)-isomer: 42%, optical purity: 100% e.e., (1R,2S)-isomer/(1S,2S)-isomer=99.8/0.2).

EXAMPLE 53

Isolation of (1R,2S)-1-(4-hydroxyphenyl)-2-amino-1-propanol hydrochloride

A methanol solution (4,468 mg; (1R,2S)-isomer: 2.77 mmol) of (1R,2S)-1-(4-hydroxyphenyl)-2-amino-1-propanol hydrochloride described in EXAMPLE 49 was condensed under a reduced pressure to obtain a viscous oily substance. To this substance, 1 mL of ethanol and 20 mL of acetonitrile were added, and the mixture was stirred for 30 minutes at 5° C. to precipitate crystals. The crystals were filtered off under a reduced pressure to obtain white crystals of (1R,2S)-1-(4-hydroxyphenyl)-2-amino-1-propanol hydrochloride (recovery rate of (1R,2S)-isomer: 70%, optical purity: 99.4% e.e., (1R,2S)-isomer/(1S,2S)-isomer=99.4/0.6).

EXAMPLE 54

Isolation of (1R,2S)-1-(4-hydroxyphenyl)-2-amino-1-propanol hydrochloride

A methanol solution (4,468 mg; (1R,2S)-isomer: 2.77 mmol) of (1R,2S)-1-(4-hydroxyphenyl)-2-amino-1-propanol hydrochloride described in EXAMPLE 49 was condensed under a reduced pressure to obtain a viscous oily substance. To this substance, 1 mL of methanol and 10 mL of methylene chloride were added, and the mixture was stirred for 30 minutes at 5° C. to precipitate crystals. The crystals were filtered off under a reduced pressure to obtain white crystals of (1R,2S)-1-(4-hydroxyphenyl)-2-amino-1-propanol hydrochloride (recovery rate of (1R,2S)-isomer: 84%, optical purity: 99.4% e.e., (1R,2S)-isomer/(1S,2S)-isomer=99.5/0.5).

EXAMPLE 55

Isolation of (1R,2S)-1-(4-hydroxyphenyl)-2-amino-1-propanol hydrochloride

A methanol solution (4,468 mg; (1R,2S)-isomer: 2.77 mmol) of (1R,2S)-1-(4-hydroxyphenyl)-2-amino-1-propanol hydrochloride described in EXAMPLE 49 was condensed under a reduced pressure to obtain a viscous oily substance. To this substance, 1.5 mL of ethanol and 5 mL of diisopropyl ether were added, and the mixture was stirred for 30 minutes at 5° C. to precipitate crystals. The crystals were filtered off under a reduced pressure to obtain white crystals of (1R,2S)-1-(4-hydroxyphenyl)-2-amino-1-propanol hydrochloride (recovery rate of (1R,2S)-isomer: 44%, optical purity: 99.4% e.e., (1R,2S)-isomer/(1S,2S)-isomer 99.5/0.5).

EXAMPLE 56

Isolation of (1R,2S)-1-(4-hydroxyphenyl)-2-amino-1-propanol hydrochloride

A methanol solution (4,468 mg; (1R,2S)-isomer: 2.77 mmol) of (1R,2S)-1-(4-hydroxyphenyl)-2-amino-1-propanol hydrochloride described in EXAMPLE 49 was condensed under a reduced pressure to obtain a viscous oily substance. To this substance, 1.5 mL of isopropanol and 5 mL of ethyl acetate were added, and the mixture was stirred for 30 minutes at 5° C. to precipitate crystals. The crystals were filtered off under a reduced pressure to obtain white crystals of (1R,2S)-1-(4-hydroxyphenyl)-2-amino-1-propanol hydrochloride (recovery rate of (1R,2S)-isomer: 46%, optical purity: 99.4% e.e., (1R,2S)-isomer/(1S,2S)-isomer=99.4/0.6).

EXAMPLE 57

Isolation of (1R,2S)-1-(4-hydroxyphenyl)-2-amino-1-propanol hydrochloride

A methanol solution (4,468 mg; (1R,2S)-isomer: 2.77 mmol) of (1R,2S)-1-(4-hydroxyphenyl)-2-amino-1-propanol hydrochloride described in EXAMPLE 49 was condensed under a reduced pressure to obtain a viscous oily substance. To this substance, 1.5 mL of isopropanol and 5 mL of methylene chloride were added, and the mixture was stirred for 30 minutes at 5° C. to precipitate crystals. The crystals were filtered off under a reduced pressure. White crystals of (1R,2S)-1-(4-hydroxyphenyl)-2-amino-1-propanol hydrochloride (recovery rate of (1R,2S)-isomer: 74%, optical purity: 99.0% e.e., (1R,2S)-isomer/(1S,2S)-isomer=99.3/0.7) were obtained.

SYNTHETIC EXAMPLE OF OPTICALLY ACTIVE β-AMINO ALCOHOL SALT (7) FROM OPTICALLY ACTIVE α-SUBSTITUTED AMINOKETONE SALT (5)

EXAMPLE 58

Process for synthesizing (1S,2R)-1-(4-hydroxyphenyl)-2-amino-1-propanol hydrochloride A solution of 1.980 g (5 mmol) of (2R)-1-[4-(benzyloxy)phenyl]-2-[((1R)-phenylethyl)amino]-1-propanone hydrochloride (99.4% d.e.) synthesized as in EXAMPLE 15 and 500 mg of 10% Pd/C (containing 50% of water) in 20 mL of ethanol and 5 mL of water was stirred under a hydrogen atmosphere at 1 atm and 40° C. for 20 hours. After the catalyst was filtered off, the solvents were distilled off under a reduced pressure to obtain 1.3281 g of a light-yellow, oily substance. To this substance, 30 mL of ethanol was added and condensed again. Subsequently, 1.5 mL of methanol and 15 mL of methylene chloride were added, and the resulting mixture was stirred at 5° C. for 30 minutes to precipitate crystals. The crystals were filtered off under a reduced pressure. White crystals of (1S,2R)-1-(4-hydroxyphenyl)-2-amino-1-propanol hydrochloride were obtained as a result (747.8 mg, isolation yield :72%). The optical purity and the diastereomer ratio of this substance were determined by the method set forth in EXAMPLE 22. The optical purity was 100% e.e. The ratio, (1S,2R)-isomer/(1R,2R)-isomer, was 97.8/2.2.

SYNTHETIC EXAMPLE OF OPTICALLY ACTIVE β-AMINO ALCOHOL SALT (7) FROM OPTICALLY ACTIVE α-SUBSTITUTED AMINOKETONE SALT (5)

EXAMPLE 59

Process for Synthesizing (1R,2S)-1-(4-hydroxyphenyl)-2-amino-1-propanol methanesulfonate A solution of 911 mg (2 mmol) of (2S)-1-[4-(benzyloxy)phenyl]-2-[((1R)-phenylethyl)amino]-1-propanone methanesulfonate (98.4% d.e.) synthesized as in EXAMPLE 3 911 mg of 10% Pd/C (containing 50% of water) in 10 mL of ethanol was stirred under a hydrogen atmosphere at 1 atm and 40° C. for 20 hours. After the catalyst was filtered off, the solvents were distilled off under a reduced pressure to obtain 652.4 mg of a light-yellow, oily substance. To this substance, 1 mL of ethanol and 5 mL of methylene chloride were added, and the resulting mixture was stirred at 5° C. for 30 minutes to precipitate crystals. The crystals were filtered off under a reduced pressure. White crystals of (1R,2S)-1-(4-hydroxyphenyl)-2-amino-1-propanol methanesulfonate were obtained as a result (449.8 mg, isolation yield: 85%). The optical purity and the diastereomer ratio of this substance were determined by the method set forth in EXAMPLE 22. The optical purity was 98.6% e.e. The ratio, (1R,2S)-isomer/(1S,2S)-isomer, was 90.4/9.6.

$^1$H-NMR (DMSO, 400 MHz/ppm): δ 0.92 (3H, d), 2.35 (3H, s), 3.32 (1H, m), 4.75 (1H, brs), 5.85 (1H, d), 6.75 (2H, d), 7.14 (2H, d), 7.78 (3H, brs), 9.38 (1H, s)

INDUSTRIAL APPLICABILITY

The present invention can provide a practical method for easily producing an optically active β-amino alcohol useful as a pharmaceutical intermediate from an inexpensive, readily available starting material.

The invention claimed is:

1. A process for producing an optically active α-substituted aminoketone represented by formula (4):

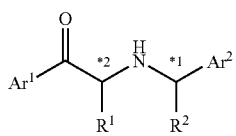
(4)

(wherein $Ar^1$ and $Ar^2$ each independently represent a substituted or unsubstituted $C_6$-$C_{15}$ aryl group, $R^1$ represents a $C_1$-$C_{12}$ alkyl or $C_7$-$C_{12}$ aralkyl group, $R^2$ represents a $C_1$-$C_{12}$ alkyl group *1 and *2 each represent an asymmetric carbon atom) or an optically active α-substituted aminoketone salt represented by formula (5):

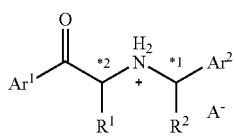
(5)

(wherein $Ar^1$, $Ar^2$, $R^1$, $R^2$, *1, and *2 are the same as above, and $A^-$ represents a counter anion), the process comprising the steps of:

reacting an α-substituted ketone represented by formula (1):

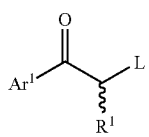
(1)

(wherein $Ar^1$ and $R^1$ are the same as above, and L represents a leaving group) with an optically active amine represented by formula (2):

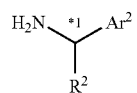
(2)

(wherein $Ar^2$, $R^2$, and *1 are the same as above) to yield a mixture of diastereomers of an optically active α-substituted aminoketone represented by formula (3):

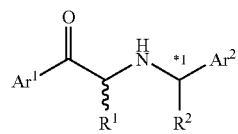
(3)

(wherein $Ar^1$, $Ar^2$, $R^1$, $R^2$, and *1 are the same as above); and isolating one diastereomer from the mixture after optionally yielding salts of the diastereomers with an acid.

2. The process according to claim 1, wherein L is a halogen atom.

3. The process according to claim 2, wherein the halogen atom is a chlorine atom or bromine atom.

4. The process according to claim 1 wherein $Ar^2$ is a phenyl group or a p-methoxyphenyl group; and $R^2$ is a methyl group.

5. The process according to claim 1, wherein $R^1$ is a methyl group or an ethyl group.

6. The process according to claim 1, wherein, in the step of isolating the diastereomer from the mixture of the diastereomers of the optically active α-substituted aminoketone represented by formula (3), a crystallization method, a chromatographic method, or a distillation method is employed.

7. The process according to claim 1, wherein, in the step of isolating the diastereomer from the mixture of the diastereomers of the optically active α-substituted aminoketone represented by formula (3), the salts of the diastereomers with the acid are yielded, and the salt of one diastereomer is preferentially crystallized from a solvent.

8. The process according to claim 7, wherein the acid is sulfonic acid.

9. The process according to claim 8, wherein the sulfonic acid is methanesulfonic acid.

10. The process according to claim 7, wherein the solvent is at least one selected from the group consisting of ester solvents, ether solvents, ketone solvents, halogenated solvents, alcohol solvents, hydrocarbon solvents, nitrile solvents, and water.

11. The process according to claim 7, wherein the solvent is ethyl acetate, acetone, or dimethoxyethane.

12. The process according to claim 1, wherein, in formula (4) or (5), the absolute configuration at *2 is S and the absolute configuration at *1 is R; or the absolute configuration at *2 is R and the absolute configuration at *1 is S.

13. The process according to claim 7, wherein the acid is hydrogen halide.

14. The process according to claim 13, wherein the hydrogen halide is hydrogen chloride or hydrogen bromide.

15. The process according to claim 7, wherein the solvent is an alcohol solvent or water.

16. The process according to claim 7, wherein the solvent is ethanol or a mixture of ethanol and water.

17. The process according to claim 13, wherein, in formula (4) or (5), the absolute configuration at *2 is R and the absolute configuration at *1 is R; or the absolute configuration at *2 is S and the absolute configuration at *1 is S.

18. A process for producing an optically active β-substituted amino alcohol represented by formula (6) or a salt thereof:

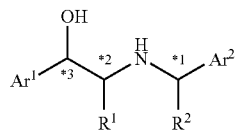

(wherein $Ar^1$, $Ar^2$, $R^1$, $R^2$, *1, and *2 are the same as in formula (4) of claim 1, and *3 represents an asymmetric carbon atom), comprising a step of stereoselectively reducing an optically active α-substituted aminoketone represented by formula (4) of claim 1 produced by the process of claim 1 or an optically active α-substituted aminoketone salt represented by formula (5) of claim 1 produced by the process of claim 1.

19. The process according to claim 18, wherein the step of stereoselectively reducing comprises selectively reducing an anti-isomer using a boron compound in methanol, ethanol, or a mixture of ethanol and water.

20. The process according to claim 19, wherein the boron compound is sodium borohydride.

21. The process according to claim 18, wherein, in formula (6), the absolute configuration at *2 is S, the absolute configuration at *1 is R, and the absolute configuration at *3 is R; or the absolute configuration at *2 is R, the absolute configuration at *1 is R, and the absolute configuration at *3 is S; or the absolute configuration at *2 is R, the absolute configuration at *1 is S, and the absolute configuration at *3 is S; or the absolute configuration at *2 is S, the absolute configuration at *1 is S, and the absolute configuration at *3 is R.

22. A process for producing an optically active α-substituted aminoketone represented by formula (4):

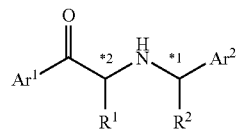

(wherein $Ar^1$ and $Ar^2$ each independently represent a substituted or unsubstituted $C_6$-$C_{15}$ aryl group, $R^1$ represents a $C_1$-$C_{12}$ alkyl or $C_7$-$C_{12}$ aralkyl group, $R^2$ represents a $C_1$-$C_{12}$ alkyl group, *1 and *2 each represent an asymmetric carbon atom) or an optically active α-substituted aminoketone salt represented by formula (5):

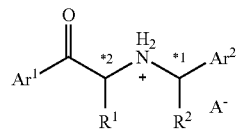

(wherein $Ar^1$, $Ar^2$, $R^1$, $R^2$, *1, and *2 are the same as above, and $A^-$ represents a counter anion), the process comprising the step of:

isolating one diastereomer from the mixture of diastereomers of an optically active α-substituted aminoketone represented by formula (3):

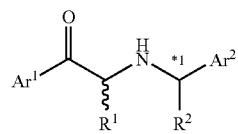

(wherein $Ar^1$, $Ar^2$, $R^1$, $R^1$, and *1 are the same as above) after optionally yielding salts of the diestereomers with an acid.

* * * * *